(12) United States Patent
Song et al.

(10) Patent No.: US 10,040,733 B2
(45) Date of Patent: Aug. 7, 2018

(54) METHOD OF RECOVERING 1,3-BUTADIENE AND METHYLETHYLKETONE FROM DEHYDRATION PRODUCTS OF 2,3-BUTANEDIOL

(71) Applicants: SK INNOVATION CO., LTD., Seoul (KR); SK GLOBAL CHEMICAL CO., LTD., Seoul (KR)

(72) Inventors: Dae Sung Song, Daejeon (KR); Sung Bum Park, Daejeon (KR); Woong Chul Shin, Daejeon (KR)

(73) Assignees: SK INNOVATION CO., LTD., Seoul (KR); SK GLOBAL CHEMICAL CO., LTD., Seoul (KR)

(*) Notice: Subject to any disclaimer, the term of this patent is extended or adjusted under 35 U.S.C. 154(b) by 245 days.

(21) Appl. No.: 14/969,047

(22) Filed: Dec. 15, 2015

(65) Prior Publication Data

US 2016/0251281 A1 Sep. 1, 2016

(30) Foreign Application Priority Data

Dec. 17, 2014 (KR) .................. 10-2014-0182351
Nov. 3, 2015 (KR) .................. 10-2015-0154075

(51) Int. Cl.
*C07C 7/08* (2006.01)
*B01D 3/00* (2006.01)
(Continued)

(52) U.S. Cl.
CPC .............. *C07C 7/08* (2013.01); *B01D 3/002* (2013.01); *B01D 3/143* (2013.01); *B01D 3/40* (2013.01);
(Continued)

(58) Field of Classification Search
CPC combination set(s) only.
See application file for complete search history.

(56) References Cited

U.S. PATENT DOCUMENTS 1,841,055 A    1/1932  Reppe et al.
2,454,447 A *  11/1948 Harney, Jr. ............. C07C 45/82
                                                       203/17
(Continued)

FOREIGN PATENT DOCUMENTS

EP    2952498 A1 * 12/2015 .......... B01J 27/1806
GB    2538940 A  * 12/2016 ............... C07C 1/24
(Continued)

OTHER PUBLICATIONS

Duan et al. "Efficient production of 1,3-butadiene in the catalytic dehydration of 2,3-butanediol", Applied Catalysis A: General, vol. 491, Feb. 5, 2015, pp. 163-169.*
(Continued)

*Primary Examiner* — In Suk C Bullock
*Assistant Examiner* — Ali Z Fadhel
(74) *Attorney, Agent, or Firm* — Abelman, Frayne & Schwab

(57) ABSTRACT

Disclosed is a method of efficiently separating 1,3-butadiene and methylethylketone, which are compounds of interest, from byproducts or impurities in the dehydration products of 2,3-butanediol so as to recover the compounds of interest at high purity.

19 Claims, 16 Drawing Sheets

(51) Int. Cl.
   *B01D 3/14* (2006.01)
   *B01D 3/40* (2006.01)
   *B01D 53/14* (2006.01)
   *C07C 7/06* (2006.01)
   *C07C 7/09* (2006.01)
   *C07C 45/81* (2006.01)
   *C07C 45/82* (2006.01)
   *C07C 45/84* (2006.01)
   *B01D 53/00* (2006.01)
   *C07C 1/24* (2006.01)
   *C12P 7/18* (2006.01)

(52) U.S. Cl.
   CPC ....... *B01D 53/002* (2013.01); *B01D 53/1418* (2013.01); *B01D 53/1487* (2013.01); *C07C 1/24* (2013.01); *C07C 7/06* (2013.01); *C07C 7/09* (2013.01); *C07C 45/81* (2013.01); *C07C 45/82* (2013.01); *C07C 45/84* (2013.01); *B01D 2252/103* (2013.01); *B01D 2256/24* (2013.01); *B01D 2257/702* (2013.01); *B01D 2257/708* (2013.01); *C12P 7/18* (2013.01); *Y02E 50/343* (2013.01)

(56) References Cited

U.S. PATENT DOCUMENTS

| | | | |
|---|---|---|---|
| 4,166,771 A * | 9/1979 | Haskell | C07C 7/08 203/58 |
| 6,444,096 B1 * | 9/2002 | Barnicki | C07C 45/80 203/43 |
| 8,252,150 B1 * | 8/2012 | Hsu | B01D 3/40 203/50 |
| 2007/0256920 A1 * | 11/2007 | Kanauchi | B01D 3/40 203/2 |
| 2010/0298621 A1 * | 11/2010 | Bridges | C07C 7/005 585/810 |
| 2012/0045807 A1 | 2/2012 | Simpson et al. | |
| 2012/0226087 A1 * | 9/2012 | Kostova | C07C 7/04 585/810 |
| 2014/0121437 A1 * | 5/2014 | Schwint | C07C 7/08 585/810 |
| 2015/0166445 A1 * | 6/2015 | Kiss | B01D 3/002 203/13 |
| 2016/0221904 A1 * | 8/2016 | Sakami | C07C 1/24 |
| 2016/0229765 A1 * | 8/2016 | Tsukamoto | C07C 1/24 |
| 2016/0355450 A1 * | 12/2016 | Grune | C07C 5/48 |

FOREIGN PATENT DOCUMENTS

| | | | |
|---|---|---|---|
| KR | 20120079584 | 7/2012 | |
| KR | 1287167 | 8/2012 | |
| KR | 2012009818 | 9/2012 | |
| WO | WO-2012157495 A1 * | 11/2012 | C07C 5/48 |

OTHER PUBLICATIONS

Hilmen, "Separation of Azeotropic Mixtures: Tools for Analysis and Studies on Batch Distillation Operation", Thesis, Norwegian University of Science and Technology Department of Chemical Engineering, Nov. 2000, p. 21-35.*

Bourns, et al., "The Catalytic Action of Aluminum Silicates," Can. J. Res. 25b:80-89 (1947).

* cited by examiner

FIG.2b

|  | 200 | 201 | 210 |
|---|---|---|---|
| Temperature C | 180 | 52 | 81 |
| Pressure kg/sqcmg | 0.9 | 0.8 | 3.5 |
| Vapor Frac | 1 | 1 | 0 |
| Mass Flow kg/hr | 12500 | 4603 | 7897 |
| Mass Flow kg/hr |  |  |  |
| 1BUTENE | 37.875 | 37.191 | 0.684 |
| 13BD | 3548.25 | 3449.42 | 98.83 |
| 2BUTENE | 42 | 41.069 | 0.931 |
| AA | 3.75 | 2.363 | 1.387 |
| 2MPA | 706.125 | 172.039 | 534.086 |
| MEK | 4161.5 | 783.558 | 3377.942 |
| C-HEXANE |  |  |  |
| H2O | 3830.875 | 116.715 | 3714.16 |
| 2MPO | 10.125 | 0.461 | 9.664 |
| ACETOIN | 3.375 | 0.035 | 3.34 |
| 23BDO | 28 | 0.006 | 27.994 |
| HEAVIES | 128.125 | 0.006 | 128.119 |
| NMP |  |  |  |
| Mass Frac |  |  |  |
| 1BUTENE | 0.003 | 0.008 | 87 PPM |
| 13BD | 0.284 | 0.749 | 0.013 |
| 2BUTENE | 0.003 | 0.009 | 118 PPM |
| AA | 300 PPM | 513 PPM | 176 PPM |
| 2MPA | 0.056 | 0.037 | 0.068 |
| MEK | 0.333 | 0.170 | 0.428 |
| C-HEXANE |  |  |  |
| H2O | 0.306 | 0.025 | 0.470 |
| 2MPO | 810 PPM | 100 PPM | 0.001 |
| ACETOIN | 270 PPM | 8 PPM | 423 PPM |
| 23BDO | 0.002 | 1 PPM | 0.004 |
| HEAVIES | 0.010 | 1 PPM | 0.016 |
| NMP |  |  |  |

FIG. 3b

|  | 303 | 304 | 305 | 309 | 312 | 313 | 411 |
|---|---|---|---|---|---|---|---|
| Temperature C | 93 | 39 | 60 | 37 | 138 | 38 | 38 |
| Pressure kg/sqcmg | 4.0 | 3.9 | 3.9 | 3.2 | 3.5 | 4.2 | 4.5 |
| Vapor Frac | 1 | 1 | 0 | 0 | 0 | 0 | 0 |
| Mass Flow kg/hr | 4415 | 3809 | 8256 | 15 | 165 | 3628 | 7650 |
| Mass Flow kg/hr | | | | | | | |
| 1BUTENE | 38.417 | 37.84 | 0.576 | 0.001 | < 0.001 | 37.839 | trace |
| 13BD | 3571.405 | 3544.808 | 26.598 | 0.122 | 0.165 | 3544.519 | trace |
| 2BUTENE | 42.808 | 41.96 | 0.848 | 0.001 | 0.011 | 41.947 | trace |
| AA | 20.819 | 0.359 | 20.474 | 0.002 | trace | 0.357 | 0.015 |
| 2MPA | 154.249 | 0.475 | 154.521 | trace | 0.475 | trace | 0.746 |
| MEK | 330.858 | 1.011 | 330.611 | trace | 1.011 | trace | 0.765 |
| C-HEXANE | 185.472 | 163.785 | 21.687 | trace | 163.785 | trace | trace |
| H2O | 71.227 | 18.648 | 7633.909 | 14.993 | trace | 3.656 | 7581.33 |
| 2MPO | 0.072 | 0.004 | 0.367 | | 0.004 | | 0.3 |
| ACETOIN | 0.003 | 0.011 | 4.155 | | 0.011 | | 4.162 |
| 23BDO | < 0.001 | < 0.001 | 59.696 | | < 0.001 | | 59.696 |
| HEAVIES | trace | 0.003 | 2.983 | | 0.003 | | 2.986 |
| NMP | | | | | | | |
| Mass Frac | | | | | | | |
| 1BUTENE | 0.009 | 0.010 | 70 PPM | 57 PPM | 2 PPM | 0.010 | trace |
| 13BD | 0.809 | 0.931 | 0.003 | 0.008 | 0.001 | 0.977 | trace |
| 2BUTENE | 0.010 | 0.011 | 103 PPM | 67 PPM | 69 PPM | 0.012 | trace |
| AA | 0.005 | 94 PPM | 0.002 | 100 PPM | 2 PPB | 99 PPM | 2 PPM |
| 2MPA | 0.035 | 125 PPM | 0.019 | trace | 0.003 | trace | 98 PPM |
| MEK | 0.075 | 266 PPM | 0.040 | trace | 0.006 | trace | 100 PPM |
| C-HEXANE | 0.042 | 0.043 | 0.003 | trace | 0.990 | trace | trace |
| H2O | 0.016 | 0.005 | 0.925 | 0.992 | trace | 0.001 | 0.991 |
| 2MPO | 16 PPM | 1 PPM | 45 PPM | | 24 PPM | | 39 PPM |
| ACETOIN | 667 PPB | 3 PPM | 503 PPM | | 64 PPM | | 544 PPM |
| 23BDO | 3 PPB | 107 PPB | 0.007 | | 2 PPM | | 0.008 |
| HEAVIES | trace | 772 PPB | 361 PPM | | 18 PPM | | 390 PPM |
| NMP | | | | | | | |

FIG. 4b

| | 316 | 317 | 320 | 323 | 325 | 334 | 335 | 344 | OFFGAS2 | P-BD |
|---|---|---|---|---|---|---|---|---|---|---|
| Temperature C | 59 | 112 | 43 | 43 | 120 | 100 | 131 | 38 | 58 | 40 |
| Pressure kg/sqcmg | 6.2 | 5.9 | 3.9 | 5.0 | 4.2 | 4.5 | 0.5 | 6.5 | 5.5 | 3.7 |
| Vapor Frac | 1 | 0 | 0 | 0 | 0 | 1 | 0 | 0 | 1 | 0 |
| Mass Flow kg/hr | 3628 | 32774 | 223 | 3556 | 31015 | 2019 | 28996 | 29219 | 73 | 3552 |
| Mass Flow kg/hr | | | | | | | | | | |
| 1BUTENE | 37.839 | 12.87 | 0.005 | 12.866 | 3.811 | 3.811 | trace | 0.005 | 24.974 | 12.866 |
| 13BD | 3544.519 | 3528.905 | 2.02 | 3526.758 | 1969.413 | 1969.315 | 0.098 | 2.119 | 17.733 | 3526.729 |
| 2BUTENE | 41.947 | 12.189 | 0.005 | 12.185 | 7.412 | 7.412 | trace | 0.005 | 29.764 | 12.185 |
| AA | 0.357 | 1.576 | 0.022 | 0.356 | 1.566 | 0.368 | 1.198 | 1.22 | 0.001 | 0.356 |
| 2MPA | trace | <0.001 | trace | trace | <0.001 | trace | <0.001 | <0.001 | trace | trace |
| MEK | trace | <0.001 | trace | trace | <0.001 | <0.001 | <0.001 | <0.001 | trace | trace |
| C-HEXANE | trace | trace | trace | trace | trace | trace | trace | trace | trace | trace |
| H2O | 3.656 | 4382.41 | 220.839 | 3.735 | 4196.201 | 38.366 | 4157.835 | 4379.554 | 0.8 | 0.355 |
| 2MPO | | 0.002 | trace | trace | 0.002 | <0.001 | 0.002 | 0.002 | trace | trace |
| ACETOIN | | <0.001 | trace | trace | <0.001 | trace | <0.001 | <0.001 | trace | trace |
| 23BDO | | trace | | | trace | trace | trace | trace | trace | |
| HEAVIES | | trace | | | trace | trace | trace | trace | trace | |

FIG. 4b'

| | 316 | 317 | 320 | 323 | 325 | 334 | 335 | 344 | OFFGAS2 | P-BD |
|---|---|---|---|---|---|---|---|---|---|---|
| NMP Mass Frac | | 24836.463 | trace | trace | 24836.467 | 0.004 | 24836.463 | 24836.464 | < 0.001 | |
| 1BUTENE | 0.010 | 393 PPM | 22 PPM | 0.004 | 123 PPM | 0.002 | trace | 167 PPB | 0.341 | 0.004 |
| 13BD | 0.977 | 0.108 | 0.009 | 0.992 | 0.063 | 0.975 | 3 PPM | 73 PPM | 0.242 | 0.993 |
| 2BUTENE | 0.012 | 372 PPM | 22 PPM | 0.003 | 239 PPM | 0.004 | trace | 169 PPB | 0.406 | 0.003 |
| AA | 99 PPM | 48 PPM | 99 PPM | 100 PPM | 50 PPM | 182 PPM | 41 PPM | 42 PPM | 17 PPM | 100 PPM |
| 2MPA | trace | trace | trace | trace | trace | 4 PPB | trace | trace | trace | trace |
| MEK | trace | 7 PPB | trace | trace | 9 PPB | 28 PPB | 8 PPB | 8 PPB | trace | trace |
| C-HEXANE | trace | trace | trace | trace | trace | 2 PPB | trace | trace | trace | trace |
| H2O | 0.001 | 0.134 | 0.991 | 0.001 | 0.135 | 0.019 | 0.143 | 0.150 | 0.011 | 100 PPM |
| 2MPO | | 72 PPB | trace | trace | 77 PPB | 30 PPB | 81 PPB | 80 PPB | trace | trace |
| ACETOIN | | 2 PPB | trace | trace | 2 PPB | trace | 2 PPB | 2 PPB | trace | |
| 23BDO | | trace | | | trace | trace | trace | trace | trace | |
| HEAVIES | | trace | | trace | trace | trace | trace | trace | | |
| NMP | | 0.76 | | | 0.80 | 2 PPM | 0.86 | 0.85 | 4 PPM | |

FIG. 5b

|  | 316-1 | 317-1 | 318 | FUEL3 | FUEL4 | P-BD |
|---|---|---|---|---|---|---|
| Temperature C | 38 | 42 | 44 | 42 | 44 | 41 |
| Pressure kg/sqcmg | 4.0 | 3.8 | 4.0 | 3.8 | 3.5 | 3.5 |
| Vapor Frac | 0 | 0 | 0 | 0 | 0 | 0 |
| Mass Flow kg/hr | 3628 | 4 | 3426 | 199 | 58 | 3367 |
| Mass Flow kg/hr |  |  |  |  |  |  |
| 1BUTENE | 37.839 | < 0.001 | 15.932 | 21.907 | 0.019 | 15.913 |
| 13BD | 3544.519 | 0.003 | 3367.293 | 177.223 | 33.673 | 3333.62 |
| 2BUTENE | 41.947 | trace | 41.947 | < 0.001 | 24.534 | 17.414 |
| AA | 0.357 | < 0.001 | 0.355 | 0.003 | 0.009 | 0.346 |
| 2MPA | trace | trace | trace | trace | trace | trace |
| MEK | trace | trace | trace | trace | trace | trace |
| C-HEXANE | trace | trace | trace | trace | trace | trace |
| H2O | 3.656 | 3.565 | trace | 0.091 |  |  |
| 2MPO |  |  |  |  |  |  |
| ACETOIN |  |  |  |  |  |  |
| 23BDO |  |  |  |  |  |  |
| HEAVIES |  |  |  |  |  |  |
| NMP |  |  |  |  |  |  |
| Mass Frac |  |  |  |  |  |  |
| 1BUTENE | 0.010 | 32 PPM | 0.005 | 0.110 | 321 PPM | 0.005 |
| 13BD | 0.977 | 799 PPM | 0.983 | 0.890 | 0.578 | 0.990 |
| 2BUTENE | 0.012 | trace | 0.012 | 61 PPB | 0.421 | 0.005 |
| AA | 99 PPM | 14 PPM | 104 PPM | 14 PPM | 150 PPM | 103 PPM |
| 2MPA | trace | trace | trace | trace | 3 PPB | trace |
| MEK | trace | trace | trace | trace | trace | trace |
| C-HEXANE | trace | trace | trace | trace | trace | trace |
| H2O | 0.001 | 0.999 | trace | 456 PPM |  |  |
| 2MPO |  |  |  |  |  |  |
| ACETOIN |  |  |  |  |  |  |
| 23BDO |  |  |  |  |  |  |
| HEAVIES |  |  |  |  |  |  |
| NMP |  |  |  |  |  |  |

FIG. 6b

| | 401 | 402 | 403 |
|---|---|---|---|
| Temperature C | 40 | 40 | 40 |
| Pressure kg/sqcmg | 3.2 | 3.2 | 3.2 |
| Vapor Frac | 0 | 0 | 0 |
| Mass Flow kg/hr | 17756 | 5020 | 12736 |
| Mass Flow kg/hr | | | |
| 1BUTENE | 3.713 | 3.492 | 0.221 |
| 13BD | 473.063 | 448.899 | 24.165 |
| 2BUTENE | 5.082 | 4.741 | 0.341 |
| AA | 25.99 | 9.555 | 16.435 |
| 2MPA | 894.415 | 793.859 | 100.556 |
| MEK | 4361.368 | 2976.021 | 1385.347 |
| C-HEXANE | 303.428 | 302.857 | 0.57 |
| H2O | 11452.371 | 342.189 | 11110.183 |
| 2MPO | 10.501 | 7.587 | 2.913 |
| ACETOIN | 7.539 | 1.589 | 5.95 |
| 23BDO | 87.696 | 2.359 | 85.337 |
| HEAVIES | 131.111 | 126.843 | 4.268 |
| NMP | | | |
| Mass Frac | | | |
| 1BUTENE | 209 PPM | 696 PPM | 17 PPM |
| 13BD | 0.027 | 0.089 | 0.002 |
| 2BUTENE | 286 PPM | 944 PPM | 27 PPM |
| AA | 0.001 | 0.002 | 0.001 |
| 2MPA | 0.050 | 0.158 | 0.008 |
| MEK | 0.246 | 0.593 | 0.109 |
| C-HEXANE | 0.017 | 0.060 | 45 PPM |
| H2O | 0.645 | 0.068 | 0.872 |
| 2MPO | 591 PPM | 0.002 | 229 PPM |
| ACETOIN | 425 PPM | 317 PPM | 467 PPM |
| 23BDO | 0.005 | 470 PPM | 0.007 |
| HEAVIES | 0.007 | 0.025 | 335 PPM |
| NMP | | | |

FIG. 7b

|  | 404 | 405 | 406 | OFFGAS1 |
|---|---|---|---|---|
| Temperature C | 42 | 94 | 131 | 94 |
| Pressure kg/sqcmg | 3.2 | 1.5 | 1.8 | 1.5 |
| Vapor Frac | 0 | 0 | 0 | 1 |
| Mass Flow kg/hr | 12736 | 1782 | 10936 | 18 |
| Mass Flow kg/hr | | | | |
| 1BUTENE | 0.221 | 0.191 | trace | 0.03 |
| 13BD | 24.165 | 21.631 | trace | 2.534 |
| 2BUTENE | 0.341 | 0.298 | trace | 0.042 |
| AA | 16.435 | 15.734 | 0.021 | 0.681 |
| 2MPA | 100.556 | 98.329 | 1.067 | 1.16 |
| MEK | 1385.347 | 1372.892 | 1.094 | 11.361 |
| C-HEXANE | 0.57 | 0.556 | trace | 0.015 |
| H2O | 11110.183 | 270.307 | 10837.701 | 2.175 |
| 2MPO | 2.913 | 2.477 | 0.428 | 0.008 |
| ACETOIN | 5.95 | < 0.001 | 5.95 | trace |
| 23BDO | 85.337 | < 0.001 | 85.337 | trace |
| HEAVIES | 4.268 | trace | 4.268 | trace |
| NMP | | | | |
| Mass Frac | | | | |
| 1BUTENE | 17 PPM | 107 PPM | trace | 0.002 |
| 13BD | 0.002 | 0.012 | trace | 0.141 |
| 2BUTENE | 27 PPM | 167 PPM | trace | 0.002 |
| AA | 0.001 | 0.009 | 2 PPM | 0.038 |
| 2MPA | 0.008 | 0.055 | 98 PPM | 0.064 |
| MEK | 0.109 | 0.770 | 100 PPM | 0.631 |
| C-HEXANE | 45 PPM | 312 PPM | trace | 807 PPM |
| H2O | 0.872 | 0.152 | 0.991 | 0.121 |
| 2MPO | 229 PPM | 0.001 | 39 PPM | 465 PPM |
| ACETOIN | 467 PPM | 86 PPB | 544 PPM | 6 PPB |
| 23BDO | 0.007 | 17 PPB | 0.008 | trace |
| HEAVIES | 335 PPM | trace | 390 PPM | trace |
| NMP | | | | |

FIG. 8b

| | 402 | 405 | 407 | 503 | 504 | 510 | 511 | FUEL1 | FUEL2 | MK-CHEX | P-MEK |
|---|---|---|---|---|---|---|---|---|---|---|---|
| Temperature C | 40 | 94 | 57 | 67 | 67 | 106 | 72 | 53 | 175 | 30 | 69 |
| Pressure kg/sqcmg | 3.2 | 1.5 | 1.5 | 0.8 | 0.8 | 3.5 | -0.2 | -0.4 | -0.3 | 2.0 | -0.3 |
| Vapor Frac | 0 | 0 | 0 | 1 | 0 | 0 | 0 | 0 | 0 | 0 | 0 |
| Mass Flow kg/hr | 5020 | 1782 | 6802 | 1250 | 597 | 4956 | 4235 | 720 | 147 | 0 | 4089 |
| Mass Flow kg/hr | | | | | | | | | | | |
| 1BUTENE | 3.492 | 0.191 | 3.683 | 3.678 | 0.005 | trace | trace | trace | | | |
| 13BD | 448.899 | 21.631 | 470.53 | 469.455 | 1.074 | trace | trace | trace | | | |
| 2BUTENE | 4.741 | 0.298 | 5.039 | 5.03 | 0.009 | trace | trace | trace | | | |
| AA | 9.555 | 15.734 | 25.289 | 22.585 | 2.702 | trace | trace | trace | | | |
| 2MPA | 793.859 | 98.329 | 892.188 | 187.544 | 4.626 | 700.025 | 0.424 | 699.588 | < 0.001 | | 0.423 |
| MEK | 2976.021 | 1372.892 | 4348.914 | 199.102 | 35.087 | 4114.729 | 4094.25 | 20.574 | 8.188 | | 4086.061 |
| C-HEXANE | 302.857 | 0.556 | 303.413 | 303.428 | 0.033 | 0.248 | trace | 0.248 | | 0.295 | |
| H2O | 342.189 | 270.307 | 612.496 | 58.815 | 553.689 | trace | trace | trace | | | |
| 2MPO | 7.587 | 2.477 | 10.064 | 0.076 | 0.032 | 9.956 | 9.956 | trace | 7.912 | | 2.044 |
| ACETOIN | 1.589 | < 0.001 | 1.589 | 0.002 | 0.026 | 1.561 | 1.561 | trace | 1.56 | | 0.001 |
| 23BDO | 2.359 | < 0.001 | 2.359 | < 0.001 | 0.017 | 2.342 | 2.342 | trace | 2.342 | | trace |
| HEAVIES | 126.843 | trace | 126.843 | trace | < 0.001 | 126.842 | 126.842 | trace | 126.842 | | trace |

FIG. 8b'

| | 402 | 405 | 407 | 503 | 504 | 510 | 511 | FUEL1 | FUEL2 | MK-CHEX | P-MEK |
|---|---|---|---|---|---|---|---|---|---|---|---|
| NMP Mass Frac | | | | | | | | | | | |
| 1BUTENE | 696 PPM | 107 PPM | 541 PPM | 0.003 | 9 PPM | trace | trace | | | | |
| 13BD | 0.089 | 0.012 | 0.069 | 0.376 | 0.002 | trace | trace | trace | | | |
| 2BUTENE | 944 PPM | 167 PPM | 741 PPM | 0.004 | 16 PPM | trace | trace | trace | | | |
| AA | 0.002 | 0.009 | 0.004 | 0.018 | 0.005 | trace | trace | | | | |
| 2MPA | 0.158 | 0.055 | 0.131 | 0.150 | 0.008 | 0.141 | 100 PPM | 0.971 | 265 PPB | | 104 PPM |
| MEK | 0.593 | 0.770 | 0.639 | 0.159 | 0.059 | 0.830 | 0.967 | 0.029 | 0.056 | | 0.999 |
| C-HEXANE | 0.060 | 312 PPM | 0.045 | 0.243 | 55 PPM | 50 PPM | trace | 344 PPM | | 1.000 | |
| H2O | 0.068 | 0.152 | 0.090 | 0.047 | 0.927 | 1 PPB | trace | 8 PPB | | | |
| 2MPO | 0.002 | 0.001 | 0.001 | 61 PPM | 54 PPM | 0.002 | 0.002 | trace | 0.054 | | 500 PPM |
| ACETOIN | 317 PPM | 86 PPB | 234 PPM | 2 PPM | 43 PPM | 315 PPM | 369 PPM | trace | 0.011 | | 313 PPB |
| 23BDO | 470 PPM | 17 PPB | 347 PPM | 58 PPB | 29 PPM | 473 PPM | 553 PPM | trace | 0.016 | | trace |
| HEAVIES | 0.025 | trace | 0.019 | 2 PPB | 116 PPB | 0.026 | 0.030 | trace | 0.864 | | trace |
| NMP | | | | | | | | | | | |

METHOD OF RECOVERING 1,3-BUTADIENE AND METHYLETHYLKETONE FROM DEHYDRATION PRODUCTS OF 2,3-BUTANEDIOL

BACKGROUND OF THE INVENTION

1. Technical Field

This application claims the benefit of Korean Patent Application No. 10-2014-0182351 filed on Dec. 17, 2014 and Korean Patent Application No. 10-2015-0154075 filed on Nov. 3, 2015, the content of each are incorporated herein by reference in its entirety.

The present invention relates to a method of separating and recovering 1,3-butadiene and methylethylketone from dehydration products of 2,3-butanediol. More particularly, the present invention relates to a method of efficiently separating 1,3-butadiene and methylethylketone, which are compounds of interest, from byproducts or impurities in the dehydration products of 2,3-butanediol so as to recover the compounds of interest at high purity.

2. Description of the Related Art 1,3-butadiene is used in various manufacturing sectors, including those of hydrocarbon fuels, polymers, synthetic rubber, plastics, and fibers, and methylethylketone is widely utilized as a solvent in the synthesis of various fine chemicals. However, these compounds, especially 1,3-butadiene, which is mainly prepared from petroleum-based energy sources (e.g. steam cracking), suffers from problems including limited resource availability, regional disparities, and environmental pollution. Furthermore, as more gas crackers using abundant gas resources are built, C4 oil fractions are reduced, and thus increased yield of 1,3-butadiene is required. Recently, the demand for 1,3-butadiene is drastically increasing because synthetic rubber is widely utilized in the manufacture of various electric products and vehicles and because of the rapid economic growth in China and the like. Also, the demand for methylethylketone is increasing in China in the fields of plastics, fibers, construction, furniture, vehicles, and electronics, and product costs are continuously increasing.

With the goal of solving the problems, thorough research is ongoing into the full or partial replacement of petroleum resources with biomass. In this regard, the preparation of 1,3-butadiene and methylethylketone through the dehydration of 2,3-butanediol is known. 2,3-butanediol is known to be produced through fermentation by microorganisms (e.g. *Bacillus polymyxa* or *Klebsiella pneumonia*).

The reaction mechanism for converting a polyhydroxy compound such as 2,3-butanediol into a diolefin such as 1,3-butadiene has been known since the 1930s (e.g. U.S. Pat. No. 1,841,055; Bourns A N, Nicholss R V V, The catalytic action of aluminium silicates. I. The dehydration of 2,3-butanediol and 2-butanone over activated Morden bentonite. Can J Research 25b:80-89 (1947)). Based on recent research results, 2,3-butanediol is converted into 1-buten-3-ol through dehydration and then additionally dehydrated, thereby producing 1,3-buradiene, and 2,3-butanediol is converted into 2,3-dimethyl oxirane through dehydration, whereby methylethylketone is produced.

For dehydration, a variety of catalysts, for example, a cesium oxide-silica composite (Korean Patent Application Publication No. 2012-0099818), a niobium-silicate-phosphate composite (Korean Patent Application Publication No. 2012-0079584), etc. are disclosed. In this regard, the use of a phosphate compound catalyst, such as hydroxyapatite and/or calcium pyrophosphate, to increase the selectivity and yield of 1,3-butadiene and/or methylethylketone, is known these days (Korean Patent No. 1287167).

In the conventional techniques, attention is paid to dehydration catalysts and/or reaction conditions for converting 2,3-butanediol into 1,3-butadiene and/or methylethylketone, but specific methods of efficiently recovering highly pure 1,3-butadiene and/or methylethylketone from the dehydration products have not been devised. Upon real-world operation, the dehydration products of 2,3-butanediol essentially include a variety of byproducts (especially by-oxygenates) and water, and thus the separation of the compounds of interest at high yield and high efficiency is required. Specifically, the dehydration products include a variety of oxygen-containing compounds (carbonyl compounds such as aldehyde, alcohol, etc.), water resulting from dehydration and the like, in addition to 1,3-butadiene and/or methylethylketone.

In this regard, the standards for 1,3-butadiene and methylethylketone in related fields are shown in Tables 1 and 2 below.

TABLE 1

| Items | Standard | Test method |
|---|---|---|
| Conjugated diene, wt % | Min. 99.0 | ASTM D 2593 |
| Peroxide, wt ppm | Max. 10 | ASTM D 1022 |
| Acetylene, wt ppm | Max. 400 | ASTM D 2593 |
| Carbonyl compound (acetaldehyde), wt ppm | Max. 100 | ASTM D 4423 |
| Butadiene dimer, wt % | Max. 0.2 | ASTM D 2426 |
| Non-volatile, wt % | Max. 0.1 | ASTM D 1025 |
| Total sulfur, wt ppm | Max 10 | ASTM D 2784 or UOP 791 |

TABLE 2

| Items | Standard | Test method |
|---|---|---|
| Color (Pt—Co) | Max. 10 | ASTM D4176 |
| Water, wt % | Max. 0.05 | ASTM D1364 |
| Acidity (CH$_3$COOH), mg/kg | Max. 30 | ASTM D1613 |
| Methylethylketone (dry basis), wt % | Min. 99.75 | — |
| Alcohol impurities, wt % | Max. 0.05 | — |
| Ethylacetate, wt % | Max. 0.15 | — |
| Acetone, wt % | Max. 0.1 | — |

However, since various compounds produced via the dehydration reaction include compounds having similar boiling points, the separation efficiency thereof is low when typical distillation alone is conducted, undesirably resulting in low yield. Furthermore, it is difficult to satisfy the standards of highly pure 1,3-butadiene and methylethylketone.

For these reasons, processes of effectively separating 1,3-butadiene and methylethylketone as compounds of interest from various byproducts of the dehydration of 2,3-butanediol so as to recover the compounds of interest at high yield and high purity are not specifically known in the related art.

SUMMARY OF THE INVENTION

Accordingly, embodiments of the present disclosure aim to provide a method of efficiently recovering highly pure 1,3-butadiene and methylethylketone from the dehydration products of 2,3-butanediol.

A first aspect of the present invention provides a method of recovering 1,3-butadiene and methylethylketone from the dehydration products of 2,3-butanediol, comprising:

a) providing a vapor stream comprising 1,3-butadiene, butene, methylethylketone, aldehyde, alcohol and water, as the dehydration products of 2,3-butanediol;

b) cooling the vapor stream, thus separating a 1,3-butadiene-rich first vapor stream and a methylethylketone-rich first liquid stream;

c) transferring the first vapor stream to a 1,3-butadiene purification unit, thus recovering 1,3-butadiene;

d) subjecting the first liquid stream to phase separation, thus obtaining a second liquid stream as an organic phase and a third liquid stream as an aqueous solution phase, separately from c);

e) separating the third liquid stream into (i) a water-rich bottom stream and (ii) a fourth liquid stream comprising a methylethylketone-water azeotropic mixture as an overhead stream;

f) combining the second liquid stream and the fourth liquid stream, and removing water from the combined liquid stream, thus obtaining a fifth liquid stream; and g) recovering methylethylketone from the fifth liquid stream.

A second aspect of the present invention provides a method of preparing 1,3-butadiene and methylethylketone from 2,3-butanediol, comprising:

a') fermenting a substrate comprising biomass, CO or $CO_2$ by a strain, thus producing 2,3-butanediol;

b') subjecting the 2,3-butanediol to dehydration in the presence of an alkaline earth metal phosphate catalyst, thus providing a vapor stream comprising 1,3-butadiene, butene, methylethylketone, aldehyde, alcohol and water;

c') cooling the vapor stream, thus separating a 1,3-butadiene-rich first vapor stream and a methylethylketone-rich first liquid stream;

d') transferring the first vapor stream to a 1,3-butadiene purification unit, thus recovering 1,3-butadiene;

e') subjecting the first liquid stream to phase separation, thus obtaining a second liquid stream as an organic phase and a third liquid stream as an aqueous solution phase, separately from d');

f') separating the third liquid stream into (i) a water-rich bottom stream and (ii) a fourth liquid stream comprising a methylethylketone-water azeotropic mixture as an overhead stream;

g') combining the second liquid stream and the fourth liquid stream, and removing water from the combined liquid stream, thus obtaining a fifth liquid stream; and h') recovering methylethylketone from the fifth liquid stream.

In an embodiment, the dehydration products of 2,3-butanediol may contain at least about 3.5 wt % of 1,3-butadiene and at least about 3.5 wt % of methylethylketone.

In an embodiment, the method may further comprise scrubbing the 1,3-butadiene-rich first vapor stream, obtained in b), using a water-containing scrubbing fluid, before being fed to c). As such, the water-containing scrubbing fluid may be at least a portion of the water-rich bottom stream separated in e).

In an exemplary embodiment, c) may comprise:

c1) fractionating the first vapor stream, thus obtaining an overhead stream including 1,3-butadiene and butene;

c2) transferring the overhead stream obtained in c1) to an extractive distillation column, thus separating a raffinate including butene as an overhead stream and an extract including 1,3-butadiene as a bottom stream; and c3) separating a mixture comprising 1,3-butadiene and water from the extract including 1,3-butadiene using at least one stripper.

In an exemplary embodiment, a solvent used in the extractive distillation column in c2) may include an N-methyl-2-pyrrolidone (NMP) aqueous solution, and a concentration (water content) of the NMP aqueous solution may exceed about 8 wt %, particularly about 12 wt %, and more particularly about 15 wt %.

In an exemplary embodiment, the method may further comprise transferring the mixture comprising 1,3-butadiene and water, separated in c3), to a purification column, so that water is removed as an overhead stream and 1,3-butadiene is recovered as a bottom stream. As such, the water content in the recovered 1,3-butadiene may be about 100 wt ppm or less, and particularly about 80 wt ppm or less.

In an alternative embodiment, c) may comprise:

c'1) fractionating the first vapor stream, thus obtaining an overhead stream including 1,3-butadiene and butene;

c'2) transferring the overhead stream obtained in c'1) to a distillation column, thus separating, as an overhead stream, a mixture comprising 1-butene and 1,3-butadiene, and as a bottom stream, a mixture comprising 1,3-butadiene and 2-butene;

c'3) recovering the mixture comprising 1-butene and 1,3-butadiene from the overhead stream separated in c2); and c'4) transferring the bottom stream separated in c2) to a 1,3-butadiene recovery column, thus separating 1,3-butadiene as an overhead stream and 2-butene as a bottom stream, and recovering the 1,3-butadiene.

In an exemplary embodiment, f) may be performed using an entrainer in an azeotropic distillation column (ADC), so that water is removed as an overhead stream and the fifth liquid stream is obtained as a bottom stream. As such, examples of the entrainer may include hexane, cyclohexane and/or heptane, and particularly useful is cyclohexane.

In an exemplary embodiment, g) may comprise:

g1) fractionating the fifth liquid stream, thus separating a methylethylketone-containing bottom stream and an overhead stream containing a compound having a boiling point lower than that of methylethylketone; and g2) fractionating the methylethylketone-containing bottom stream obtained in g1), thus separating an overhead stream including methylethylketone and a bottom stream including a compound having a boiling point higher than that of methylethylketone.

In an exemplary embodiment, the compound having a boiling point lower than that of methylethylketone in g1) may include 2-methylpropanal (2-MPA).

In an exemplary embodiment, the compound having a boiling point higher than that of methylethylketone in g2) may include 2-methylpropanol (2-MPO).

According to embodiments of the present disclosure, the effective separation of 1,3-butadiene and methylethylketone, which are compounds of interest, from considerable amounts of byproducts (especially by-oxygenates) and other impurities in the dehydration products of 2,3-butanediol can be realized, separately obtaining highly pure 1,3-butadiene and methylethylketone. In particular, the process according to embodiments of the present disclosure can overcome the technical limitations of conventional processes in which the separation of 1,3-butadiene from petroleum-based oil fractions, especially C4 oil fractions (mixtures), cannot be applied because of the properties of the dehydration products of 2,3-butanediol. Thereby, since 1,3-butadiene and methylethylketone, which satisfy the requirements of the art, can be obtained, limitations on supply sources of 1,3-butadiene and methylethylketone can be overcome, thus expecting a wide range of applications thereof in future.

BRIEF DESCRIPTION OF THE DRAWINGS

FIGS. 2A and 2B illustrate the quencher according to an exemplary embodiment and the details of the related streams, respectively;

FIGS. 3A and 3B illustrate the scrubber and 1,3-butadiene (BD) fractionator according to an exemplary embodiment and the details of the related streams, respectively;

FIGS. 4A and 4B illustrate the purification of 1,3-butadiene (BD) using an extractive distillation column in the process according to an embodiment of the present invention and the details of the related streams, respectively;

FIGS. 5A and 5B illustrate the purification of 1,3-butadiene (BD) using a simple distillation column in the process according to an alternative embodiment and the details of the related streams, respectively;

FIGS. 6A and 6B illustrate the decanter according to an exemplary embodiment and the details of the related streams, respectively;

FIGS. 7A and 7B illustrate the water removal unit according to an exemplary embodiment and the details of the related streams, respectively; and FIGS. 8A and 8B illustrate the methylethylketone (MEK) purification unit according to an exemplary embodiment and the details of the related streams, respectively.

DESCRIPTION OF SPECIFIC EMBODIMENTS

Figure 1:
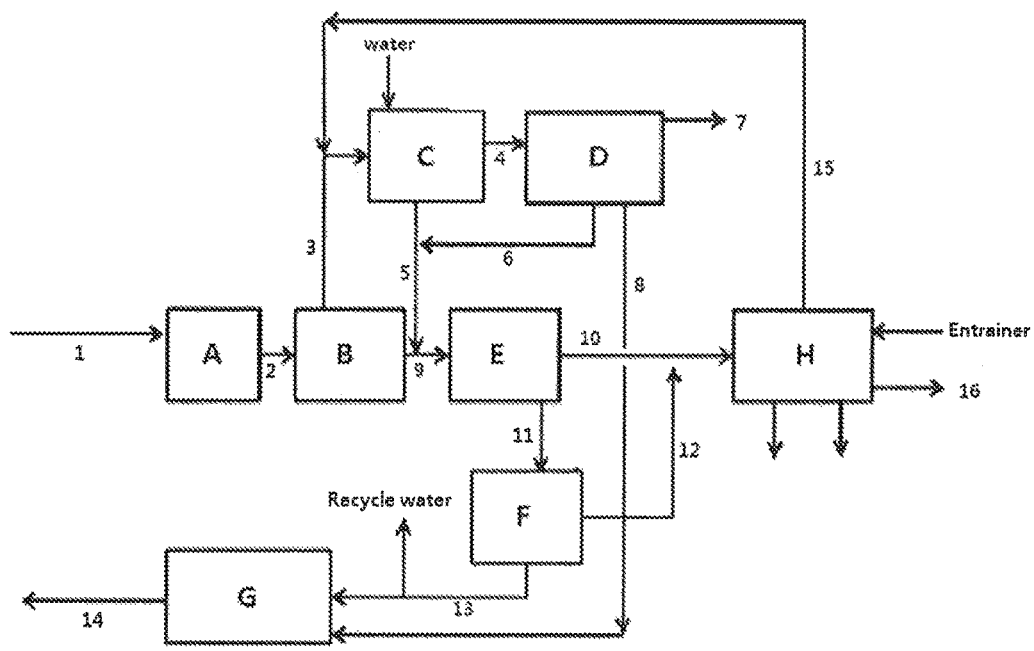
FIG. 1 schematically illustrates the process of separating and recovering 1,3-butadiene and methylethylketone from the dehydration products of 2,3-butanediol according to an embodiment of the present invention.

Hereinafter, a detailed description will be given of embodiments of the present invention with reference to the appended drawings. Such embodiments are merely illustrative, but are not to be construed as limiting the present invention.

2,3-Butanediol (BDO)

In an embodiment, 2,3-butanediol is used as a starting material. 2,3-butanediol, having four carbon chains and two reactive sites, is known to be a key compound useful in the synthesis of fine chemicals, etc. 2,3-butanediol is referred to as 2,3-butylene glycol, dimethylene glycol, 2,3-dihydroxybutane, or butan-2,3-diol, with a boiling point of about 177° C. As used herein, "2,3-butanediol" is typically represented by Chemical Formula 1 below, and includes stereoisomers such as (R,R), (S,S) and meso forms, and may be conceptually understood to include all racemic isomers, diastereomers, and highly pure optical isomers.

[Chemical Formula 1]

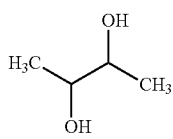

In the present disclosure, 2,3-butanediol, which is not limited to specific supply sources or is derived from various preparation methods or supply sources, may be used as a starting material. In specific embodiments, 2,3-butanediol may be typically produced through fermentation. Examples of usable strains (bacteria) may include *Klebsiella pneumoniae, Bacillus polymyxa, Enterobacter aerogenes, Bacillus subtilis, Aeromonas hydrophila, Serratia*, etc., and biomass may be used as a carbon source. Recently, the technique for preparation of 2,3-butanediol through gas fermentation is known, and broadly means a biological process for converting CO or $CO_2$ into low carbon fuel or chemicals.

In an embodiment, 2,3-butanediol may be prepared through gas fermentation using carbon monoxide as a substrate and as a fermentation strain, for example, *C. autoethanogenum, C. ljungdahlii, C. ragsdalei*, etc. The preparation of 2,3-butanediol through gas fermentation is specifically disclosed in U.S. Patent Application Publication No. 2012/0045807, which is hereby incorporated by reference into the present specification.

Dehydration of 2,3-Butanediol

In an embodiment, 2,3-butanediol is dehydrated in the presence of a catalyst, and is thus converted into 1,3-butadiene and methylethylketone, as represented in Scheme 1 below.

[Scheme 1]

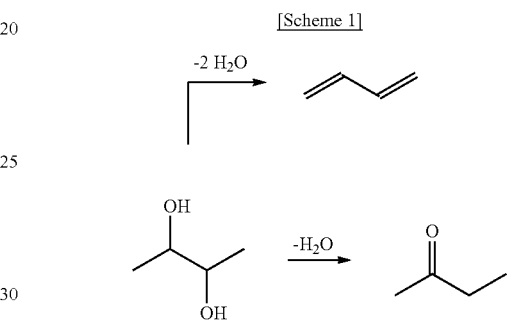

The catalyst for dehydration of 2,3-butanediol is typically exemplified by an alkaline earth metal phosphate catalyst.

In an embodiment, 2,3-butanediol may be used in the form of a pure material or solution (e.g. aqueous solution). In particular, when a 2,3-butanediol aqueous solution is used as the dehydration reactant, the inactivation of the catalyst may be prevented during the dehydration, and the reaction rate may be controlled so as to prevent a rapid reaction. Furthermore, when a 2,3-butanediol aqueous solution, which is typically obtained through fermentation, is used as the dehydration reactant, the investment in the fermentation unit may be reduced. In an exemplary embodiment, the upper limit of water content in the 2,3-butanediol aqueous solution may be set to about 80 wt %, particularly about 50 wt %, and more particularly about 30 wt %.

In a specific embodiment, an alkaline earth metal phosphate catalyst, especially a calcium phosphate catalyst, may be used for dehydration. The calcium phosphate catalyst may be crystalline or amorphous, and the value (molar ratio) of Ca/P in the catalyst may be about 0.5 to 2.0, particularly about 0.7 to 1.7, and more particularly about 1.0 to 1.67. The catalyst may be more specifically exemplified by a non-crystalline (amorphous) calcium phosphate catalyst having a Ca/P ratio of about 1.2 to 1.3.

The properties of usable forms of calcium phosphate catalyst are illustrated in Table 3 below.

TABLE 3

| Calcium phosphate | Ca/P ratio | pH interval |
|---|---|---|
| Hydroxyapatite ($Ca_{10}(PO_4)_6(OH)_2$) | 1.50 to 1.67 | >5 |
| Amorphous calcium phosphate | 1.33 to 1.67 | — |
| Calcium pyrophosphate ($Ca_2P_2O_7$) | about 1.00 | — |

The calcium phosphate catalyst has both acidic and basic properties. In the hydroxyapatite structure, the amount of Ca in the catalyst is increased, thus exhibiting the basic properties relatively strongly. On the other hand, catalysts having a calcium pyrophosphate structure manifest the acidic properties relatively strongly. The amorphous calcium phosphate catalyst having a Ca/P ratio of about 1.2 to 1.3 is configured such that the amounts of acid and base are controlled.

The method of preparing the catalyst, especially the calcium phosphate (i.e. amorphous calcium phosphate) catalyst, may be illustratively described below.

Specifically, an alkali is reacted with a phosphoric acid-containing solution, thus preparing an alkali phosphate aqueous solution. As such, the phosphoric acid of the phosphoric acid-containing solution may include at least one selected from among ortho-phosphoric acid ($H_3PO_4$), pyrophosphoric acid ($H_4P_2O_7$), tripolyphosphoric acid ($H_5P_3O_{10}$, and tetrapolyphosphoric acid ($H_6P_4O_{13}$). Particularly useful is phosphoric acid or pyrophosphoric acid, and more particularly pyrophosphoric acid may be used.

In an exemplary embodiment, the alkali may include a strong base such as NaOH or a weak base such as ammonia. Particularly useful is a weak base, and more particularly useful is ammonia. When ammonia is used, an amorphous calcium phosphate catalyst may be prepared. The use of the amorphous calcium phosphate catalyst further increases the conversion of 2,3-butanediol and the selectivity of compounds of interest (1,3-butadiene and methylethylketone).

Upon the preparation of the alkali phosphate aqueous solution, the molar ratio of phosphoric acid relative to the alkali may be, for example, about 0.1 to 4, particularly about 0.5 to 2, and more particularly about 1 to 1.67. The pH of the alkali phosphate aqueous solution may be, for example, about 4 to 13, particularly about 5 to 11, and more particularly about 6 to 10.

Then, the alkali phosphate aqueous solution thus prepared is added with a calcium precursor aqueous solution, yielding a calcium phosphate slurry. The calcium precursor may include calcium chloride, calcium nitrate, and calcium acetate, which may be used alone or in combination. The molar ratio of Ca/P may be, for example, about 0.5 to 4, particularly about 0.7 to 2, and more particularly about 1 to 1.7.

Then, the calcium phosphate slurry thus prepared is thermally treated. This thermal treatment functions to increase the specific surface area of phosphate particles and to increase the activity. Before the thermal treatment, the calcium phosphate slurry may be dried in the form of cakes (e.g. about 50 to 200° C., and particularly about 70 to 150° C.). The thermal treatment temperature may be about 300 to 1000° C., particularly about 350 to 800° C., and more particularly about 400 to 700° C. Also, the thermal treatment time may be, for example, about 1 to 10 hr, particularly about 2 to 8 hr, and more particularly about 4 to 6 hr. In an exemplary embodiment, a molding process, which is known in the art, may be performed (e.g. pellet form), before or after the thermal treatment.

In an alternative embodiment, the dehydration catalyst may be exemplified by a solid acid catalyst, such as a zeolite catalyst, a silica-alumina catalyst, a zirconia catalyst, a Mania catalyst, a heteropoly acid catalyst, etc.

Examples of the zeolite catalyst may include H—Y, H—BEA, H-ZSM-5, H-MOR, H-MFI, H-FAU, and mixtures thereof. The molar ratio of $SiO_2/Al_2O_3$ may be about 10 to 300, and particularly about 20 to 50.

The heteropoly acid may include at least one selected from among 12-molybdophosphoric acid ($H_3PMo_{12}O_{40}$), 12-tungstophosphoric acid ($H_3PW_{12}O_{40}$), 12-silicotungstic acid ($H_4SiW_{12}O_{40}$), 12-molybdotungstophosphoric acid ($H_3PMo_{12-x}W_xO_{40}$, x=0 to 12), 12-molybdovanadophosphoric acid ($H_{3+x}PMo_{12-x}V_xO_{44}$, x=0 to 12), and 12-tungstovanadophosphoric acid ($H_{3+x}PW_{12-x}V_xO_{40}$, x=0 to 12).

The catalyst should not be understood as being limited, so long as the products resulting from the dehydration of 2,3-butanediol using the catalyst may be applied in the process, as will be described later.

The dehydration conditions are not particularly limited, and a fixed-bed reactor or a batch reactor may be used. The reaction temperature may be for example about 200 to 800° C., particularly about 250 to 500° C., and more particularly about 300 to 400° C. The reaction pressure may be for example about 100 bar or less, particularly about 0.5 to 20 bar, and more particularly about 1 to 10 bar.

The batch reaction may be carried out for 0.1 to 50 hr, and particularly about 0.2 to 10 hr. On the other hand, for a continuous reaction, the space velocity may be for example about 0.01 to 10 $hr^{-1}$, particularly about 0.05 to 5 $hr^{-1}$, and more particularly about 0.1 to 3 $hr^{-1}$.

Through the dehydration of 2,3-butanediol, not only 1,3-butadiene and methylethylketone, but also light impurities (e.g. 1-butene, 2-butene, etc.), byproducts including oxygen-containing compounds (e.g. acetaldehyde, 2-MPA, 3-buen-2-ol, 2-butanol, 2-MPO, 3-hydroxy-2-butanone, etc.), heavy components, and a large amount of water may be produced, and may be provided in a vapor phase. The dehydration products of 2,3-butanediol may be composed of 1,3-butadiene, butene, methylethylketone, aldehyde, alcohol, and water.

In an embodiment, the amount of 1,3-butadiene in the dehydration products may be, for example, at least about 3.5 wt %, particularly about 7 to 53 wt %, and more particularly about 11 to 42 wt %. Also, the amount of methylethylketone in the products may be, for example, at least about 3.5 wt %, particularly about 7 to 53 wt %, and more particularly about 11 to 45 wt %.

The illustrative compositions for the dehydration products of 2,3-butanediol are given in Table 4 below.

TABLE 4

|  | General range (wt %) | Particular range (wt %) | More particular range (wt %) |
|---|---|---|---|
| Acetaldehyde | 0 to 0.7 | 0 to 0.35 | 0 to 0.001 |
| 1,3-Butadiene | 3.5 to 60 | 7 to 53 | 11 to 42 |
| 2-Butene | 0.01 to 7 | 0.01 to 7 | 0.07 to 3.5 |
| 1-Butene | 0.01 to 7 | 0.01 to 7 | 0.07 to 3.5 |
| 2-MPA | 0.1 to 14 | 0.01 to 7 | 0.07 to 3.5 |
| 3-Buten-2-ol | 0 to 7 | 0 to 7 | 0 to 3.5 |
| Methylethylketone | 3.5 to 60 | 7 to 53 | 11 to 45 |
| 2-Butanol | 0 to 7 | 0 to 7 | 0 to 3.5 |
| 2-MPO | 0.01 to 7 | 0.01 to 7 | 0.07 to 3.5 |
| 3-Hydroxy-2-butanone | 0 to 7 | 0 to 7 | 0 to 0.07 |
| Heavy compound | 0 to 7 | 0 to 7 | 0 to 5 |
| Water | 3.5 to 60 | 7 to 53 | 15 to 50 |

The considerable amounts of impurities in the dehydration products may have a negative influence on the downstream processes that use 1,3-butadiene and/or methylethylketone. Among light impurities, butene, such as 1-butene or 2-butene, has a small difference in boiling point from 1,3-butadiene, and thus, separation through simple distillation requires a column having a large number of stages. Furthermore, a considerable amount of water in the reaction product may realize liquid-liquid equilibrium (minimum azeotrope) with an oxygen-containing compound, including methylethylketone, and thus the separation thereof through typical distillation is not efficient. Accordingly, effective recovery (purification) of the products of interest, namely 1,3-butadiene and methylethylketone, from the dehydration products of 2,3-butanediol, is regarded as important to realize efficient overall operation of production processes and ensure price competitiveness.

Dehydration of 2,3-Butanediol and Recovery of 1,3-Butadiene and Methylethylketone Therefrom FIG. 1 schematically illustrates the process of separating and recovering 1,3-butadiene (1,3-BD) and methylethylketone (MEK) from the dehydration products of 2,3-butanediol according to an embodiment of the present invention.

This process is performed using a reactor A, a quencher B, a scrubber C, 1,3-BD purification unit D, a decanter E, a water removal unit F, a wastewater treatment unit G, and a MEK purification unit H.

a. Reactor

In the reactor A, 2,3-butanediol 1, serving as a starting material (reactant), undergoes dehydration and then a dehydration product 2 in a vapor phase (or a gas phase) is discharged. As such, the reaction product is a complicated mixture comprising not only 1,3-BD and MEK but also a plurality of byproducts and water, and may be discharged in a vapor phase at about 200 to 800° C. (particularly about 250 to 500° C., and more particularly about 300 to 400° C.). In some cases, before being fed to the quencher B, the dehydration product 2 may be primarily cooled (e.g. about 100 to 300° C.) through heat exchange with the feed 1 that is to be transferred to the reactor A. Although a small amount of impurities may be condensed in the course of heat exchange, the product is substantially provided in the form of a vapor to the downstream unit.

b. Quencher

The product 2 in a vapor phase is transferred to the quencher B and is thus separated into the overhead stream comprising a 1,3-BD-rich vapor 3 (a first vapor stream) and the bottom stream comprising a MEK-rich liquid 9 (a first liquid stream). Upon cooling, 1,3-BD, having a low boiling point, is present in a gas phase, whereas MEK, having a high boiling point (MEK b.p.: about 79.6° C.), exists in a liquid phase. The temperature of the vapor 3 may be adjusted through pumping around, and may be lowered to, for example, about 10 to 60° C. (particularly about 30 to 50° C., and more particularly about 32 to 43° C.), thereby minimizing the amounts of water and by-oxygenates in the vapor 3. As mentioned above, multiple stages are required to decrease the temperature of the vapor 3. In consideration thereof, the overhead stream (vapor) of the quencher (e.g. theoretical stage number: about 5 to 30) is primarily cooled to about 45 to 75° C. (particularly about 50 to 60° C.), and may then be additionally cooled to the above temperature range using a heat exchanger. In an exemplary embodiment, the amount of 1,3-BD in the vapor 3 is about 65 to 95 wt % (particularly about 70 to 90 wt %, and more particularly about 75 to 85 wt %), and the total amount of MEK and impurities such as butene, aldehyde and alcohol may be about 1 to 15 wt % (particularly about 2 to 12 wt %, and more particularly about 5 to 10 wt %), with the balance being water.

Meanwhile, liquid-liquid equilibrium (LLE) is realized when the MEK-rich liquid 9 is separated using the quencher B. As such, the quencher B needs to have an internal design suitable for efficient operation. The MEK-rich liquid 9 contains small amounts of light hydrocarbons (e.g. butene such as 1-butene and 2-butene, and 1,3-BD), and may also include considerable amounts of by-oxygenates and water.

In particular, since water, resulting from dehydration, may reach liquid-liquid equilibrium, that is, form a minimum azeotrope, together with MEK and by-oxygenates, it is difficult to efficiently separate them through simple distillation alone. The amount of MEK in the MEK-rich liquid and the amount of other oxygen-containing compounds depend on the operating conditions of the quencher B, for example, temperature, pressure, stage number, stage height, etc. In an exemplary embodiment, the amount of MEK in the liquid 9 may be about 20 to 80 wt % (particularly about 30 to 70 wt %, and more particularly about 40 to 60 wt %), and the amount of the other oxygen-containing compounds (aldehyde, alcohol, etc.) may be about 1 to 40 wt % (particularly about 2 to 30 wt %, and more particularly about 5 to 20 wt %), and a considerable amount of water is contained as the balance.

c. Scrubber

In an exemplary embodiment, before being transferred to the 1,3-BD purification unit D, the vapor 3, separated from the quencher B, is selectively compressed (e.g. to about 4 to 6 bar) and then fed to the scrubber C. When the vapor 3 is brought into contact with a scrubbing fluid (e.g. a water-containing scrubbing fluid, and particularly water), aldehyde (especially acetaldehyde) may be removed from the vapor. Consequently, the scrubbed vapor 4 is discharged. As such, the vapor 3 may be fed through the bottom of the scrubber C. In the case where acetaldehyde is not removed from the vapor, problems may occur in downstream processing using 1,3-BD. Since the standard for the amount of acetaldehyde in 1,3-BD, which is the product of interest, is in the range of about 100 wt ppm or less, and particularly about 80 wt ppm or less, acetaldehyde has to be removed before the vapor 3 is fed to the 1,3-BD purification unit D. In particular, the solubility of acetaldehyde in water is higher than 1,3-BD and butene (e.g. 1-butene and 2-butene) in a vapor phase, and thus acetaldehyde may be effectively removed through scrubbing using water.

In the above embodiment, the scrubbing fluid, especially the water-containing scrubbing fluid (or water) may be supplied from various sources, and may be exemplified by recycle water, which is separated from the downstream separation unit, for example, a water removal unit F. In this case, there is no need to use make-up water.

The amount of aldehyde (acetaldehyde) remaining upon scrubbing may be determined by the amount of water-containing scrubbing fluid fed to the top of the scrubber C and the operating conditions of the column. As the temperature of the scrubbing fluid is lower and the pressure of the scrubber is higher, the water solubility of acetaldehyde in the vapor 3 may increase. For example, upon scrubbing using water at about 38° C., the operating pressure may be set to about 5 bar. This pressure is set in consideration of the pressure at which the final product, i.e. 1,3-BD is liquefied, as well as ΔP of downstream processing. Although the scrubbing effect is enhanced with an increase in pressure, a compressor having two or more stages is required to increase the pressure of the vapor 3 separated from the quencher B to a predetermined level or more, whereby energy consumption is increased. Therefore, in a specific embodiment, the operating conditions of the scrubber may be appropriately controlled in the temperature range of about 30 to 80° C. (particularly about 28 to 70° C., and more particularly about 50 to 60° C.) and the pressure range of about 1 to 15 bar (particularly about 2 to 10 bar, and more particularly about 3 to 5 bar).

Through the scrubbing, by-oxygenates may also be removed from the vapor 3. Most of the by-oxygenates having high water solubility are removed as the bottom stream 5 of the scrubber C, and are then transferred to the liquid separation region, as will be described later.

d. 1,3-BD Purification Unit

In an embodiment, the scrubbed vapor 4 may be transferred to the 1,3-BD purification unit D to remove impurities other than 1,3-BD, which is the compound of interest.

In an illustrative aspect of the present disclosure, the 1,3-BD purification unit D may operate in the following two manners: (i) separation and recovery of 1,3-BD using an extractive distillation column and (ii) separation and recovery of 1,3-BD using a simple distillation column.

(i) Separation and Recovery of 1,3-BD Using Extractive Distillation Column

In an exemplary embodiment, the 1,3-BD purification unit includes a 1,3-BD fractionator, an extractive distillation column, and a stripper, and optionally a 1,3-butadiene purification column Considering the final purity of 1,3-BD, a single stripper or a plurality of strippers (e.g. first and second strippers) may be provided.

1,3-BD Fractionator

In an exemplary embodiment, the 1,3-BD fractionator functions such that heavy impurities other than 1,3-BD and butene in the scrubbed vapor 4, which is discharged as the overhead stream of the scrubber, are removed as the bottom stream 6. As such, the amount of 1,3-BD in the bottom stream 6 may be, for example, about 0.5 wt % or less, particularly about 0.3 wt % or less, and more particularly about 0.1 wt % or less. Of the vapor discharged as the overhead stream of the 1,3-BD fractionator, the amounts of 1,3-BD and butene are about 80 to 99.5 wt % (particularly about 85 to 99.3 wt %, and more particularly about 97 to 99 wt %), and about 0.5 to 20 wt % (particularly about 0.7 to 15 wt %, and more particularly about 1 to 3 wt %), respectively (when considering only 1,3-BD and butene in the vapor). The components (e.g. acetaldehyde, etc.) other than 1,3-BD and butene may be contained in trace amounts, for example, about 1000 wppm or less, or about 100 wppm or less.

The 1,3-fractionator may operate under operating conditions of a temperature of about 30 to 150° C. (particularly about 38 to 140° C., and more particularly about 45 to 130° C.), a pressure of about 2 to 8 bar (particularly, about 3 to 7 bar, and more particularly about 4 to 6 bar), a theoretical stage number of about 5 to 40 (particularly about 10 to 30, and more particularly about 5 to 25), and a reflux ratio of about 0.5 to 5 (particularly about 1 to 4, and more particularly about 2 to 3).

In an exemplary embodiment, water contained in the overhead stream of the 1,3-BD fractionator is separated as the stream 8 through the downstream separation unit (e.g. a drum or a decanter; not shown), and is then transferred to a wastewater treatment unit G, as will be described later. As such, the operating conditions of the water separation unit may be substantially the same as when the overhead stream of the 1,3-BD fractionator is obtained. On the other hand, the bottom stream 6 of the 1,3-BD fractionator may be combined with water 5 and/or MEK-rich liquid 9, discharged as the bottom stream of the scrubber C.

Extractive Distillation Column (EDC)

The overhead stream containing 1,3-BD and butene (1,3-BD-rich stream) is fed to the extractive distillation column (EDC), for example, the middle portion of the extractive distillation column, so that it may be separated into 1,3-BD and butene. Simultaneously, the extraction solvent is fed to the top of the extractive distillation column, whereby 1,3-BD, which has a high affinity for the extraction solvent, is obtained as the extract from the bottom of the column together with the solvent, whereas butene is separated (removed) as the raffinate in the overhead stream of the column. As such, the 1,3-BD-rich stream is desirably fed in the form of a gas phase based on the operating principle of the downstream extractive distillation column. For this, it is heated using a heat exchanger before being introduced to the extractive distillation column, thus obtaining the completely gasified phase.

The extractive distillation column may operate so that 1,3-BD, which is finally recovered, has a purity of at least about 99 wt %, particularly at least about 99.2 wt %, and more particularly at least about 99.3 wt %. As such, the efficiency of removal of butene in the extractive distillation column may be determined depending on the amount of extraction solvent and the operating conditions of extractive distillation column. In order to increase the solubility of 1,3-BD in the extraction solvent, the temperature of the extraction solvent is set to be as low as possible, and the pressure of the extractive distillation column is set to be as high as possible.

In a specific embodiment, the extraction solvent is used at a temperature of about 10 to 60° C. (particularly about 20 to 50° C., and more particularly about 30 to 40° C.). In this regard, as the pressure of the extractive distillation column is increased, the extraction efficiency may increase, and to prevent the oligomerization of 1,3-BD, the pressure may be set so that the temperature of the bottom stream of the column is a predetermined level or less, for example, about 125° C. or less (particularly about 120° C. or less). In an illustrative embodiment, the pressure of the extractive distillation column may range from about 4 to 10 bar (particularly about 5 to 8 bar, and more particularly about 6 to 7 bar).

The extraction solvent, which is fed to the extractive distillation column, may include a polar solvent, especially an N-alkylated solvent. Commercially available as the extraction solvent for BEU (Butadiene Extraction Unit) are acetonitrile (ACN), dimethylformamide (DMF), and N-methyl-2-pyrrolidone (NMP).

The real-world application of acetonitrile is limited because expensive materials have to be used due to the corrosion thereof. Hence, DMF and NMP may be considered as alternatives. However, DMF may cause hydrolysis with water at high temperature to produce DMA (dimethylamine), thus incurring problems in downstream processing using 1,3-BD. As such, DMA, which is typically controlled to about 1 ppm or less, is removed using a DMA extractor, and furthermore, the water content of the material fed to the inside of the column has to be adjusted to a predetermined level or less, for example, about 200 wt ppm or less. For this reason, NMP, especially an NMP aqueous solution, is used as the extraction solvent.

The extractive distillation process, which is adopted in a specific embodiment, is characterized in that an extraction solvent (aqueous solution) having a high water concentration may be used compared to a typical C4 butadiene extractive distillation process. In the typical C4 butadiene extractive distillation process, the extraction solvent may be an aqueous solution having a concentration (water concentration) of about 8 wt %, with high solubility in 1,3-BD, and the concentration thereof is known not to exceed 12 wt %. However, since the amount of 1,3-BD in the 1,3-BD-rich overhead stream, which is transferred to the extractive distillation column, is much higher than that of butene, the use of an aqueous solution (i.e. NMP aqueous solution) having a water concentration that exceeds about 8 wt %, particularly about 12 wt %, and more particularly about 15 wt % may decrease the concentration of 1,3-BD and lower the boiling point, and thus the operating temperature of the column may be lowered, thereby preventing the oligomerization of 1,3-BD. Exemplarily useful is an NMP aqueous solution comprising 85 wt % of NMP and 15 wt % of water. Also, the weight ratio of the extraction solvent and the 1,3-BD-rich overhead stream may be about 1:5 to 1:15, particularly about 1:6 to 1:12, and more particularly about 1:7 to 1:9.

In an exemplary embodiment, the extractive distillation column may be constructed such that distillation towers having about 20 to 60 stages, and particularly about 30 to 50 stages, are connected in series, and the temperature of the bottom of the column may be, for example, about 100 to 130° C., particularly about 105 to 125° C., and more particularly about 110 to 120° C. The amount of 1,3-BD in the extract, which is discharged from the bottom of the extractive distillation column, may be, for example, about 4 to 20 wt %, particularly about 6 to 15 wt %, and more particularly about 8 to 12 wt %.

Stripper

In a specific embodiment, the extract, which is separated as the bottom stream of the column, is transferred to at least one stripper, so that 1,3-BD is recovered from the extraction solvent. In an exemplary embodiment, the stripper may have a two-stage structure, that is, may include first and second strippers. The bottom stream (extract) of the extractive distillation column is separated into the overhead stream comprising 1,3-BD and the bottom stream comprising the extraction solvent in the first stripper.

As such, the bottom temperature of the first stripper is maintained at a predetermined level or less, for example, about 125° C. or less (particularly about 120° C. or less), thus preventing the polymerization of 1,3-BD. In an exemplary embodiment, the first stripper may operate under the condition that the pressure is decreased to about 3 to 6 bar (particularly about 4.5 to 5.5 bar). To ensure higher purification effects, a compressor may be used for pressurization in the course of recycling the overhead stream (i.e. purified 1,3-BD) of the second stripper to the first stripper. In this case, the operating pressure of the first stripper may be decreased, thereby reducing the load on the downstream compressor. Additionally, the first stripper may operate under conditions of a theoretical stage number of about 5 to 25 (particularly about 7 to 20, and more particularly 10 to 15) and a reflux ratio of about 0.5 to 3 (particularly about 0.8 to 2.5, and more particularly about 1 to 2).

In an exemplary embodiment, the second stripper is operated at a pressure (e.g. about 0.4 to 3 bar, and particularly about 1.5 to 2 bar) lower than the first stripper, and 1,3-BD, which is contained in the bottom stream of the first stripper, is additionally separated as the overhead stream, and is then recycled to the first stripper. As such, the recovery efficiency of 1,3-BD in the overhead stream of the second stripper may be, for example, at least about 99.99 wt %, and particularly at least about 99.995 wt %.

1,3-BD in the overhead stream of the second stripper may be recovered by recycling the overhead stream of the second stripper to the first stripper through pressurization. Thus, in the exemplary embodiment, 1,3-BD may be recovered from the overhead stream of the first stripper. As such, the second stripper may operate under conditions of a temperature of about 40 to 130° C. (particularly about 50 to 120° C., and more particularly 60 to 100° C.), a theoretical stage number of about 5 to 25 (particularly about 7 to 20, and more particularly 10 to 15), and a reflux ratio of about 0.2 to 3 (particularly about 0.8 to 2.5, and more particularly about 1 to 2).

1,3-BD Purification Column

In a specific embodiment, the overhead stream discharged from the first stripper is transferred to the 1,3-BD purification column, so that water is removed therefrom, ultimately recovering 1,3-BD 7. As such, water is removed as the overhead stream of the 1,3-BD purification column, and 1,3-BD is recovered as the bottom stream thereof, and the 1,3-BD purification column may operate at a pressure at which 1,3-BD is liquefied. In an exemplary embodiment, any method of removing water from 1,3-BD may be applied, and an adsorbent (e.g. active alumina such as F-200) may be used, or a distillation process may be adopted.

The purification column may operate under conditions of a temperature of about 30 to 50° C. (particularly about 35 to 45° C., and more particularly about 38 to 42° C.), a pressure of about 3 to 7 bar (particularly about 4 to 6 bar, and more particularly 4.5 to 5.5 bar), and a theoretical stage number of 2 to 7 (particularly 3 to 6, and more particularly 4 to 5). Furthermore, the overhead stream of the purification column is supplied to, for example, the downstream decanter, and thus undergoes phase separation in the decanter, yielding a hydrocarbon layer or an organic layer (1,3-BD), which may then be totally refluxed to the column, and the water layer may be transferred to the wastewater treatment unit, as will be described later.

In an exemplary embodiment, the water content of recovered 1,3-BD, may be, for example, about 100 wppm or less, and particularly about 80 wppm or less, and the purity of recovered 1,3-BD may be, for example, at least about 99.0%, and particularly at least about 99.9%.

(ii) Separation and Recovery of 1,3-BD Using Simple Distillation Column

In an exemplary embodiment, the 1,3-BD purification unit may include a 1,3-BD fractionator, a distillation column, and a 1,3-BD recovery column That is, a simple distillation column is used in lieu of the extractive distillation column using a solvent. The reason why the 1,3-BD purification unit including the simple distillation column is used is described below.

To prepare highly pure 1,3-BD, the use of the extractive distillation column may minimize the loss of 1,3-BD, but a solvent (extraction solvent) must essentially be used therefor, unavoidably increasing the investment cost attributable to the use of a compressor and equipment for treatment of the solvent. Furthermore, since the operating temperature of the extractive distillation column is relatively high, the amount of chemical used to prevent the oligomerization of 1,3-BD must also be increased, making it difficult to maintain or repair the units.

On the other hand, when 1,3-BD is recovered using a simple distillation process, 1,3-BD may be partially lost during the removal of 1-butene. However, if the mixture of 1,3-BD, which is discharged together with 1-butene, may be sold as the C4 oil fraction, competitiveness may be ensured in terms of investment cost compared to when using the extractive distillation column. In the purification process using the extractive distillation column, the 1,3-BD-rich stream, which is fed to the extractive distillation column via the 1,3-BD fractionator, has to be completely gasified, but this limitation is not imposed when using the simple distillation column.

1,3-BD Fractionator

In the embodiment, the 1,3-BD fractionator may operate in the same manner as described above, and the composition of the separated 1,3-BD-rich stream may be the same as above.

Distillation Column

As described above, the overhead stream containing 1,3-BD and butene (1,3-BD-rich stream), which is separated from the 1,3-BD fractionator, is transferred to the distillation column, so that the mixture comprising 1-butene and 1,3-butadiene as the overhead stream and the mixture comprising 1,3-butadiene and 2-butene as the bottom stream are separated from each other.

The distillation column may operate under conditions of a temperature of about 20 to 65° C. (particularly about 30 to 55° C., and more particularly about 40 to 45° C.), a pressure of about 1 to 8 bar (particularly about 2 to 6 bar, and more particularly 3 to 4 bar), a theoretical stage number of 55 to 125 (particularly 65 to 105, and more particularly 75 to 85), and a reflux ratio of about 50 to 180 (particularly about 80 to 140, and more particularly about 100 to 120).

The overhead stream of the distillation column may contain about 80 to 95 wt % (particularly about 82 to 92 wt %, and more particularly about 85 to 90 wt %) of 1,3-BD, and about 5 to 20 wt % (particularly about 8 to 12 wt %, and more particularly about 10 to 15 wt %) of 1-butene. As such, components (e.g. water, acetaldehyde, etc.) other than 1,3-BD and butene may be contained in trace amounts, for example, about 1000 wppm or less, or about 100 wppm or less. Furthermore, the bottom stream of the distillation column may contain about 96 to 98.5 wt % (particularly about 97 to 99 wt %, and more particularly about 97.5 to 99.5 wt %) of 1,3-BD, and about 0.5 to 3.5 wt % (particularly about 1 to 3 wt %, and more particularly about 1.5 to 2.5 wt %) of 2-butene, with the balance being 1-butene impurities.

Meanwhile, the bottom stream of the distillation column is transferred to the 1,3-BD recovery column, so that highly pure 1,3-BD as the overhead stream and 2-butene as the bottom stream are separated from each other. The separated 1,3-BD may be recovered as highly pure 1,3-BD. The 1,3-BD recovery column may operate under conditions of a temperature of about 20 to 65° C. (particularly about 30 to 55° C., and more particularly about 40 to 45° C.), a pressure of about 1 to 8 bar (particularly about 2 to 6 bar, and more particularly 3 to 4 bar), a theoretical stage number of 30 to 100 (particularly 40 to 80, and more particularly 50 to 60), and a reflux ratio of about 0.5 to 30 (particularly about 1 to 15, and more particularly about 2 to 5).

In an exemplary embodiment, when the components separated through the distillation column and the 1,3-BD recovery column have similar compositions (i.e. when Cp values are not significantly different), the overhead stream of the column is compressed and may thus be used as a heat source of a reboiler. When it is used for a heat pump in this way, the investment cost may increase due to the use of the compressor, but the use of steam in the column reboiler is obviated, and thus advantages may occur from the aspect of energy consumption.

e. Decanter

The liquid stream 9 separated in the quencher B is separated into an organic phase 10 (a second liquid stream) and an aqueous solution phase 11 (a third liquid stream) through phase separation in the decanter E. In an exemplary embodiment, the liquid stream 9 may be combined with the bottom stream 5 of the scrubber C and/or the bottom stream 6 of the 1,3-BD fractionator in the 1,3-BD purification unit D, and the stream thus combined may be fed to the decanter E.

In an exemplary embodiment, the decanter E may operate under conditions of a temperature of about 30 to 50° C. (particularly about 35 to 45° C., and more particularly about 38 to 42° C.) and a pressure of about 3 to 5 bar (particularly about 3.5 to 4.5 bar, and more particularly about 4 to 4.3 bar).

f. Water Removal Unit and Wastewater Treatment Unit

In an embodiment, the aqueous solution phase 11, separated in the decanter E, is transferred to the water removal unit F, thus separating the water-rich bottom stream 13 (composed mainly of water, and including an oxygen-containing compound) from the aqueous solution phase 11. Furthermore, at least a portion of the light gas (offgas) may be removed, and the MEK-water azeotropic mixture 12 (a fourth liquid stream) may be separated as the overhead stream of the water removal unit F.

In an exemplary embodiment, the water removal unit may operate under conditions of a temperature of about 80 to 140° C. (particularly about 90 to 135° C., and more particularly about 95 to 120° C.), a pressure of about 1 to 5 bar (particularly about 1.5 to 4 bar, and more particularly 2 to 3 bar), a theoretical stage number of about 5 to 15 (particularly, about 7 to 13, and more particularly about 9 to 11), and a reflux ratio of about 0.5 to 3 (particularly about 0.8 to 2.5, and more particularly about 1 to 2).

The amount of MEK in the water-rich bottom stream 13 removed from the water removal unit F may be, for example, about 0.05 wt % or less, particularly about 0.03 wt % or less, and more particularly about 0.01 wt % or less. As mentioned above, at least a portion of the stream 13 may be recycled to the scrubber C to thus remove the impurities such as acetaldehyde.

In a specific embodiment, the remainder of the water-rich bottom stream 13, which is not recycled to the scrubber C, may be transferred to the wastewater treatment unit G, and furthermore, may be utilized by being transferred to, for example, a water treatment system for the production of 2,3-butanediol through fermentation.

g. MEK Purification Unit

The organic phase 10 separated from the decanter E is combined with the MEK-water azeotropic mixture 12, separated as the overhead stream of the water removal unit F, and is then transferred to the MEK purification unit H (a fifth liquid stream). The MEK purification unit H includes an azeotropic distillation column (ADC), a first MEK fractionator, and a second MEK fractionator.

Azeotropic Distillation Column (ADC)

In an embodiment, an entrainer is used in the azeotropic distillation column, and thus water is removed as the overhead stream through azeotropic separation. The entrainer typically functions to form an azeotrope with any one component of the binary mixture but not to form an azeotrope with the other component. In an exemplary embodiment, the entrainer may be discharged together with water via the downstream decanter connected to the azeotropic distillation column.

In a specific embodiment, hexane, cyclohexane (c-hexane) or benzene may be used as the entrainer. As the entrainer, benzene is toxic and may thus be difficult to apply. The use of cyclohexane may result in very high separation efficiency of the MEK-water azeotropic mixture. The amount of the entrainer may be appropriately adjusted within the range of about 0.01 wt % or less, based on the combination of the organic phase 10 and the MEK-water azeotropic mixture 12.

The overhead stream 15 of the azeotropic distillation column is recycled, and may then be fed to the 1,3-BD fractionator (or the scrubber when the scrubber is provided), together with the vapor 3 discharged as the overhead stream of the quencher B. In an alternative embodiment, the entrainer may be recovered through cooling using a refrigerant, but the investment cost therefor may be increased.

Meanwhile, the overhead stream 15 of the azeotropic distillation column may contain about 10 to 35 wt % (particularly about 15 to 30 wt %, and more particularly about 20 to 25 wt %) of the entrainer, and about 0.1 to 40 wt % (particularly about 0.5 to 20 wt %, and more particularly about 1 to 10 wt %) of 1,3-BD.

In a specific embodiment, to additionally recover 1,3-BD partially contained in the overhead stream 15, the overhead stream 15 is recycled to the 1,3-BD fractionator, or to the 1,3-BD fractionator via the scrubber, whereby the entrainer and small amounts of by-oxygenates, contained in the overhead stream 15, are separated as the bottom stream of the 1,3-BD fractionator and may thus be combined with the MEK-rich liquid 9 discharged from the quencher B. The recycled entrainer may be reused in the azeotropic distillation column.

The amount of the entrainer in the bottom stream of the azeotropic distillation column may be, for example, about 1000 wt ppm or less, particularly about 100 wt ppm or less, and more particularly about 50 wt ppm or less. The bottom stream still contains by-oxygenates, in addition to MEK, and may include, for example, about 70 to 90 wt % (particularly about 75 to 85 wt %) of MEK, about 5 to 20 wt % (particularly, about 10 to 15 wt %) of 2-MPA (isobutyraldehyde), and about 0.001 to 0.5 wt % (particularly, about 0.005 to 0.1 wt %) of 2-MPO (isobutanol), with the balance being the other impurities.

The azeotropic distillation column may operate at a temperature of about 38 to 125° C., particularly about 55 to 120° C., and more particularly about 65 to 110° C. Furthermore, to decrease the capacity of the reboiler, the azeotropic distillation column may operate at about 0.5 to 5 bar, particularly about 1 to 3 bar, and more particularly near atmospheric pressure, whereby the entrainer may be contained in as large an amount as possible in the overhead stream, maximally inhibiting the loss of the entrainer (minimizing the use of make-up entrainer).

First MEK Fractionator

In an embodiment, the bottom stream of the azeotropic distillation column is transferred to the first MEK fractionator, thus separating the overhead stream from which relatively light components such as 2-MPA are removed, and the bottom stream including the mixture comprising MEK and other heavy components (including 2-MPO).

The first MEK fractionator operates under reduced pressure (e.g. about 0.4 to 0.9 bar, particularly about 0.5 to 0.8 bar, and more particularly about 0.6 to 0.7 bar). The reason for operating under reduced pressure is that the liquid and vapor curves are close to each other in the MEK-rich region of the phase diagram of MEK to 2-MPA, and thus a high reflux ratio has to be maintained, which requires a high reboiler capacity. Such problems may be solved by applying the reduced pressure.

The first MEK fractionator may operate at a temperature of about 38 to 90° C., particularly about 45 to 85° C., and more particularly about 50 to 75° C. Additionally, the theoretical stage number of the first MEK fractionator may be, for example, about 50 to 80, particularly about 55 to 70, and more particularly about 60 to 65, and the reflux ratio thereof may be, for example, about 25 to 45, particularly about 30 to 40, and more particularly about 32 to 38.

Based on the results of fractionation, the MEK recovery efficiency in the bottom stream of the first MEK fractionator may be, for example, at least about 99 wt %, particularly at least about 99.2 wt %, and more particularly at least about 99.5 wt %. Also, the amount of 2-MPA may be, for example, about 0.03 wt % or less, particularly about 0.02 wt % or less, and more particularly about 0.01 wt % or less.

Second MEK Fractionator

The bottom stream of the first MEK fractionator is transferred to the second MEK fractionator, so that highly pure MEK 16 is recovered as the overhead stream, and heavy impurities, especially 2-MPO, may be removed as the bottom stream. In order to suppress the thermal decomposition of the heavy impurities removed as the bottom stream, the second MEK fractionator may operate at a reduced pressure. In an exemplary embodiment, the second MEK fractionator may operate under conditions of a temperature of about 40 to 200° C. (particularly about 60 to 190° C., and more particularly about 65 to 180° C.), and a pressure of about 0.4 to 0.9 bar, particularly about 0.5 to 0.8 bar, and more particularly about 0.6 to 0.7 bar. Furthermore, the theoretical stage number of the second MEK fractionator may be, for example, about 7 to 20, particularly about 10 to 18, and more particularly about 15 to 17, and the reflux ratio thereof may be, for example, about 0.2 to 1, particularly about 0.4 to 0.8, and more particularly about 0.5 to 0.7.

Based on the results of fractionation, the MEK recovery efficiency in the overhead stream of the second MEK fractionator may be, for example, at least about 99.5 wt %, particularly at least about 99.7 wt %, and more particularly at least about 99.8 wt %. Also, the amount of 2-MPO may be, for example, about 0.07 wt % or less, particularly about 0.05 wt % or less, and more particularly about 0.03 wt % or less.

A better understanding of the present invention may be obtained through the following examples which are set forth to illustrate, but are not to be construed to limit the present invention.

Example 1

As illustrated in the process of FIG. 1 and the details of FIGS. 2A, 3A, 4A, 6A, 7A and 8A, recovery of highly pure 1,3-butadiene and methylethylketone from the dehydration products of 2,3-butanediol was simulated using ASPEN PLUS. The process simulation was based on 100,000 tons of 2,3-butanediol feed per year.

The dehydration of 2,3-butanediol was carried out using an amorphous calcium phosphate catalyst (Ca/P molar ratio: 1.2) under the conditions shown in Table 5 below.

TABLE 5

| Reaction Temp. | Reaction Pressure | Space velocity (WHSV) | Conversion |
|---|---|---|---|
| 360° C. | Atmospheric pressure | 0.5 hr$^{-1}$ | 100% |

TABLE 6

|  | Quencher | Scrubber | 1,3-BD fractionator |
|---|---|---|---|
| Pressure (O/H) [kg/cm$^2$g] | 0.8 | 3.9 | 3.2 |
| Temp. (O/H) [° C.] | 52 | 39 | 38 |
| Temp. (BTM) [° C.] | 80 | 60 | 136 |
| Theoretical stage number | 5 | 5 | 30 |
| Reflux ratio |  |  | 2.3 |

TABLE 7

|  | EDC | 1$^{st}$ Stripper | 2$^{nd}$ Stripper | 1,3-BD purification column |
|---|---|---|---|---|
| Pressure (O/H) [kg/cm$^2$g] | 5.5 | 3.9 | 0.5 | 3.7 |
| Temp. (O/H) [° C.] | 58 | 43 | 42 | 40 |
| Temp. (BTM) [° C.] | 112 | 120 | 130 | 44 |
| Theoretical stage number | 36 | 15 | 15 | 5 |
| Reflux ratio | 5.3 | 2.3 | 0.22 | Organic phase total reflux |

TABLE 8

|  | De-canter | Water removal unit (column) | ADC | 1$^{st}$ MEK fractionator | 2$^{nd}$ MEK fractionator |
|---|---|---|---|---|---|
| Pressure (O/H) [kg/cm$^2$ g] | 3.2 | 1.5 | 0.8 | −0.4 (Absolute pressure: 0.6 bar) | −0.3 (Absolute pressure: 0.7 bar) |
| Temp. (O/H) [° C.] | 40 | 94 | 67 | 53 | 69 |
| Temp. (BTM) [° C.] |  | 131 | 106 | 72 | 175 |
| Theoretical stage number |  | 10 | 30 | 62 | 16 |
| Reflux ratio |  | 1 | Organic phase total reflux | 36 | 0.5 |

Figure 2A:
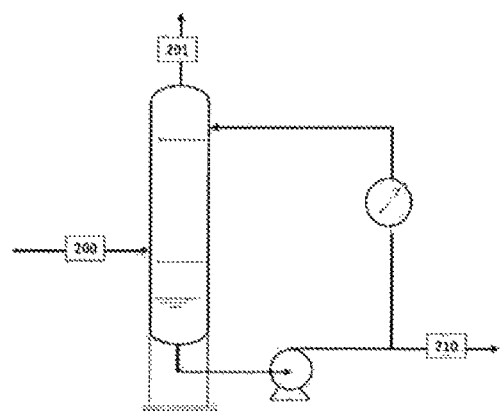

As illustrated in FIG. 2A, the dehydration products of 2,3-butanediol were fed to the quencher, and were separated into the overhead stream comprising a 1,3-BD-rich vapor 201 and the bottom stream comprising an MEK-rich liquid 210. The details (mass balance, temperature, pressure, flow rate, composition, etc.) of the inflow and outflow streams of the quencher are shown in FIG. 2B.

Figure 3A:
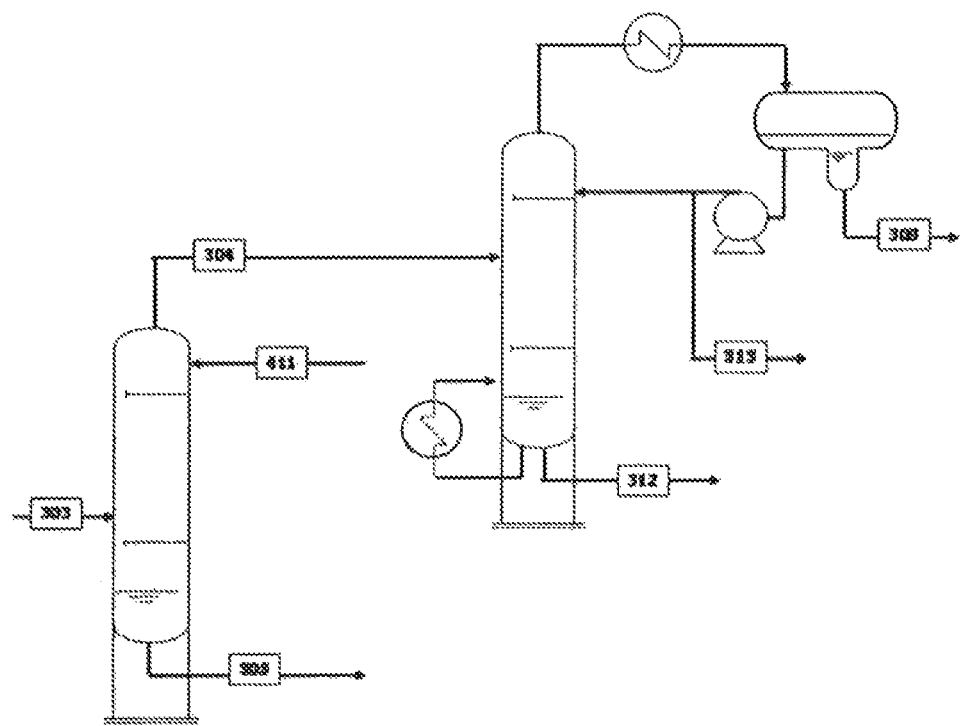

As illustrated in FIG. 3A, the stream 303 derived from the overhead stream of the quencher was scrubbed with the water-containing scrubbing fluid 411 fed from the top of the scrubber, and the overhead stream 304 of the scrubber and the bottom stream 305 thereof were discharged. Also, the overhead stream 304 was fed to the 1,3-BD fractionator and was separated into the overhead stream comprising 1,3-BD, butene and water, and the bottom stream 312 comprising heavy impurities and water. The overhead stream was transferred to the drum via the heat exchanger, whereby water 309 was separated therefrom. Furthermore, a portion of the mixture comprising 1,3-BD and butene was refluxed to the 1,3-BD fractionator, and the remainder stream 313 was transferred to the downstream unit. The details of the inflow and outflow streams of the scrubber and the 1,3-BD fractionator are shown in FIG. 3B.

Figure 4A:
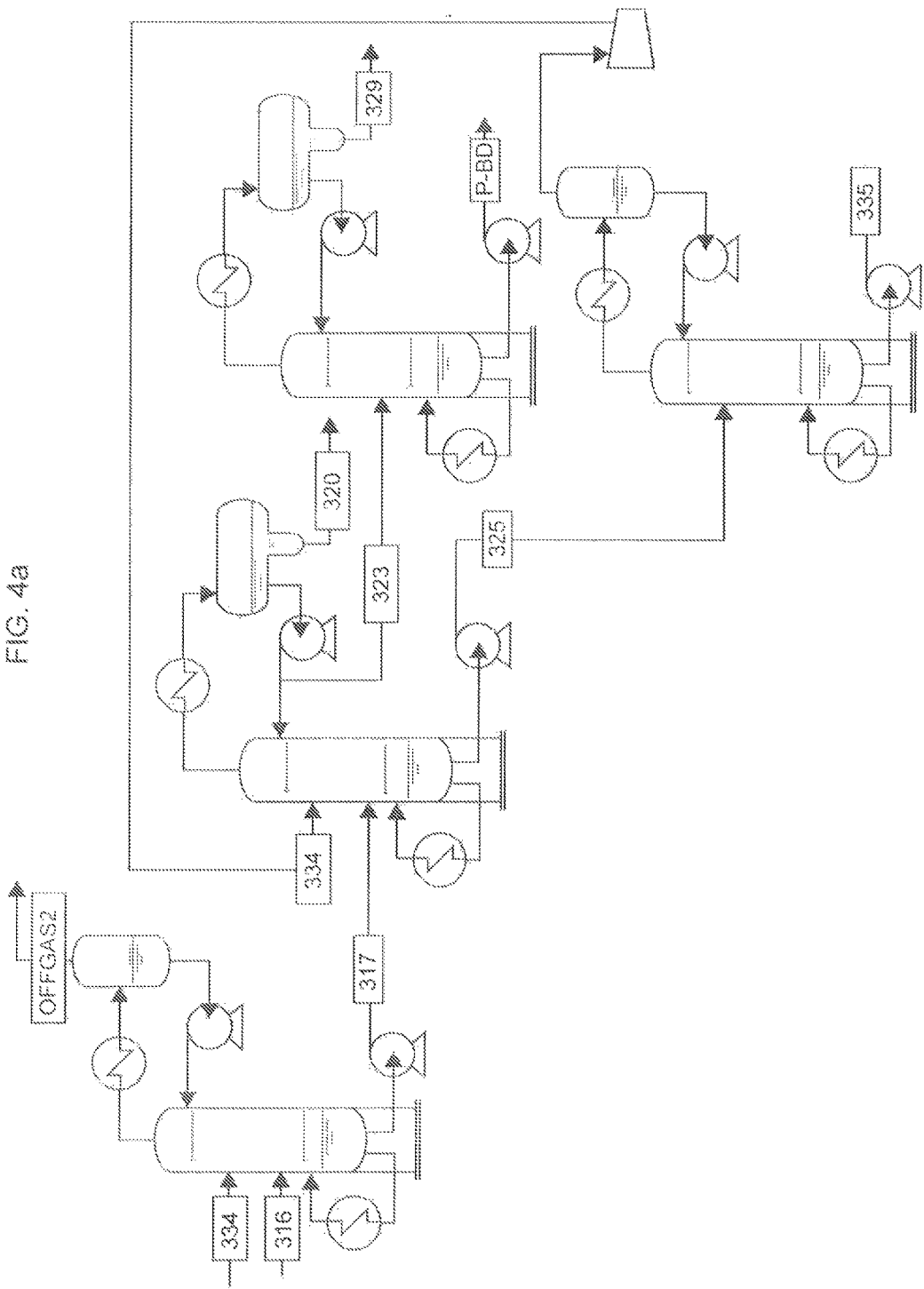

As illustrated in FIG. 4A, the stream 316 derived from the overhead stream of the 1,3-BD fractionator was fed to the extractive distillation column, together with the extraction solvent stream 344, and the raffinate containing butene was separated as the overhead stream, and was then refluxed to the extractive distillation column after the removal of offgas therefrom. The extract containing 1,3-BD was separated as the bottom stream 317.

The stream 317 was fed to the first stripper, and the overhead stream, composed mainly of 1,3-BD, was passed through the heat exchanger and then the drum, thus additionally removing water 320, after which a portion of the stream was refluxed to the first stripper, and the remainder stream 323 was transferred to the downstream 1,3-BD purification column. Meanwhile, the bottom stream 325 of the first stripper was composed mainly of the extraction solvent, and contained a small amount of 1,3-BD that was not separated in the first stripper. The stream 325 was fed to the second stripper, thus obtaining the 1,3-BD-containing stream as the overhead stream, a portion of which was then refluxed, and the remainder stream 334 was recycled to the first stripper. Furthermore, the stream 335 composed mainly of the extraction solvent was separated as the bottom stream of the second stripper and was reused in the extractive distillation column.

The stream 323 was transferred to the 1,3-BD purification column, so that water 329 was removed as the overhead stream and 1,3-BD was recovered as the bottom stream. The details of the inflow and outflow streams of the extractive distillation column, the first and second strippers and the 1,3-BD purification column are shown in FIG. 4B.

Figure 6A:
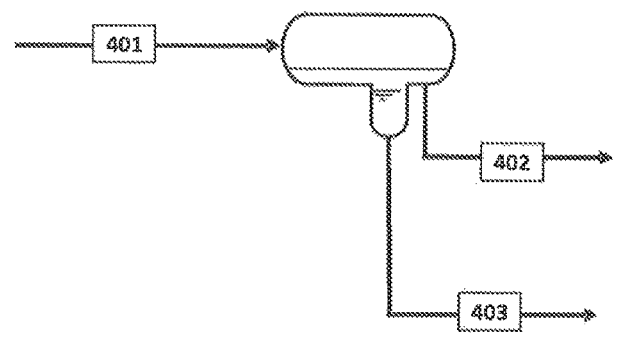

As illustrated in FIG. 6A, the stream 401 derived from the bottom stream of the quencher was transferred to the decanter and underwent phase separation, thus obtaining the organic phase 402 and the aqueous solution phase 403. The details of the inflow and outflow streams of the decanter are shown in FIG. 6B.

Figure 7A:
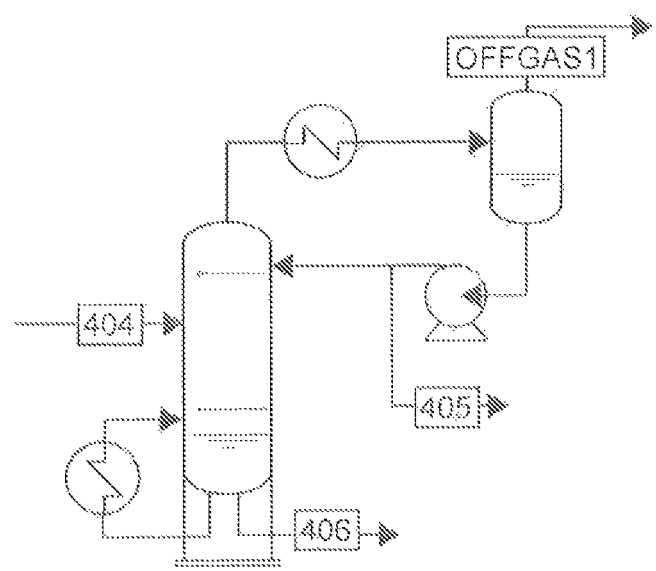

As illustrated in FIG. 7A, the stream 404 derived from the aqueous solution phase separated from the decanter was transferred to the water removal unit (water removal column), thus separating the bottom stream 406, which was composed mainly of water and partially of oxygen-containing compound. Also, the overhead stream including the MEK-water azeotropic mixture was passed through the heat exchanger, followed by removing offgas. Then, a portion of the overhead stream was refluxed to the water removal unit, and the remainder stream 405 was transferred to the downstream unit. The details of the inflow and outflow streams of the water removal unit are shown in FIG. 7B.

Figure 8A:
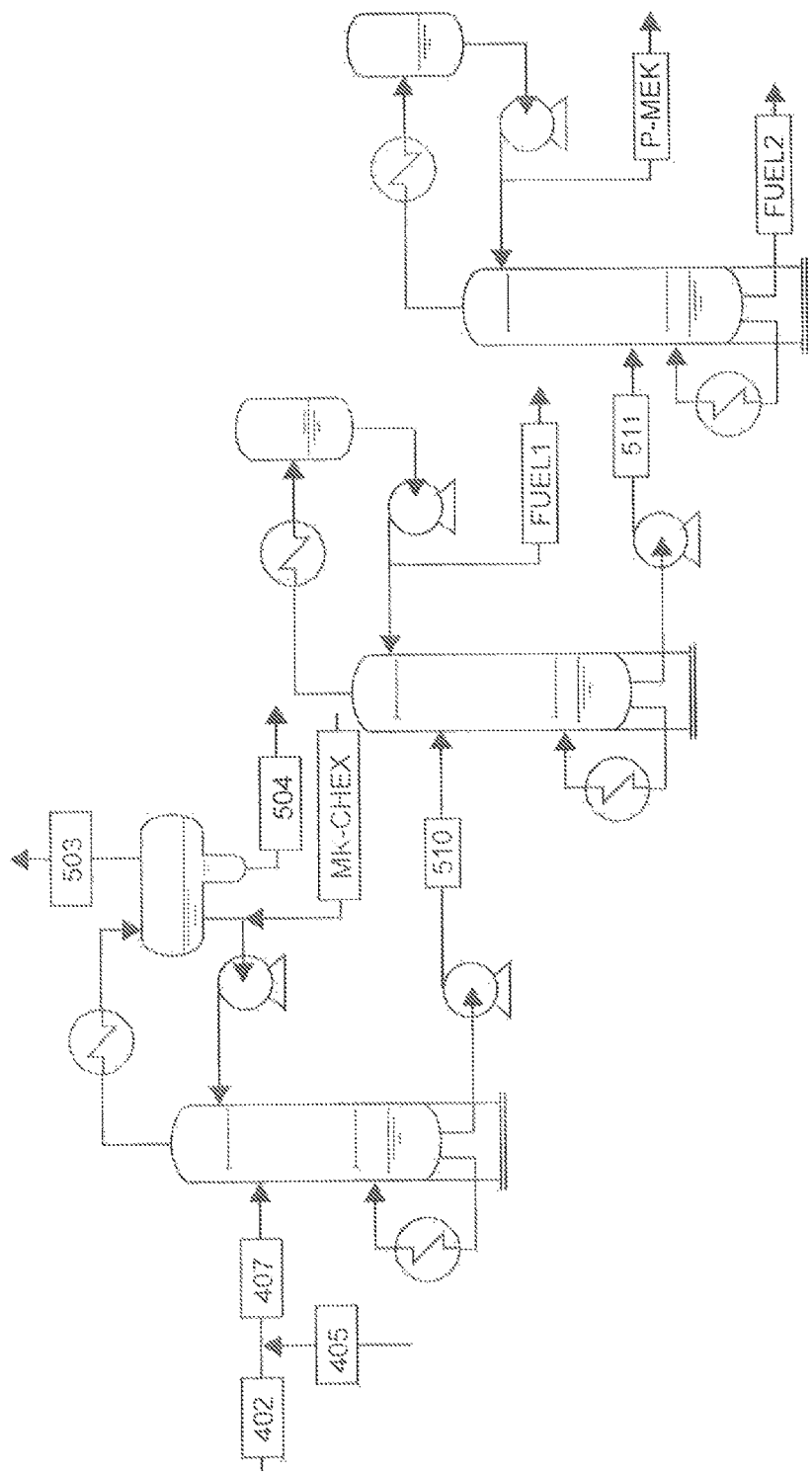

As illustrated in FIG. 8A, the stream 402 derived from the decanter was combined with the stream 405 derived from the overhead stream of the water removal unit, after which the stream 407 thus combined was fed to the azeotropic distillation column.

The overhead stream of the azeotropic distillation column was composed mainly of water and entrainer (i.e. cyclohexane), and contained 1,3-BD and by-oxygenates in small amounts. The overhead stream was transferred to the drum via the heat exchanger, and to additionally recover 1,3-BD from the overhead stream, the stream 503 was separately recycled, and the stream 504 was transferred to the wastewater treatment unit. Also, the entrainer (i.e. cyclohexane) separated from the overhead stream of the azeotropic distillation column was recycled to the azeotropic distillation column, together with the make-up entrainer, and was thus used to remove water from the stream 407.

The bottom stream 510 of the azeotropic distillation column was transferred to the first MEK fractionator, and as the overhead stream, the stream containing light components such as 2-MPA was separated, a portion of which was refluxed and the remainder of which was recovered. Separately, the bottom stream 511 of the first MEK fractionator was fed to the second MEK fractionator and thus MEK was separated as the overhead stream, a portion of which was refluxed and the remainder of which was recovered as highly pure MEK. The bottom stream of the second MEK fractionator contained heavy impurities such as 2-MPO, and was separately recovered.

The details of the inflow and outflow streams of the azeotropic distillation column, the first MEK fractionator and the second MEK fractionator are shown in FIG. 8B.

As illustrated in the above drawings, 1,3-BD and MEK, recovered from the dehydration products of 2,3-butanediol in the present example, met commercial standards.

Example 2

Figure 5A:
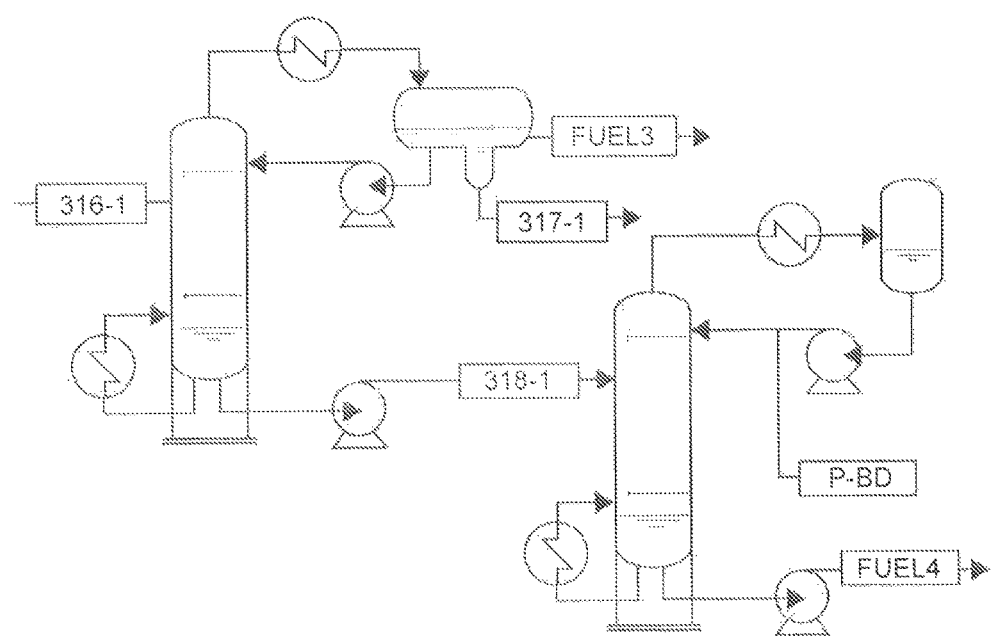

The process simulation was carried out in the same manner as in Example 1, with the exception that the simple distillation column and the 1,3-BD recovery column shown in FIG. 5A were used, in lieu of the process performed in the sequence of the extractive distillation column, first and second strippers and 1,3-BD purification column of Example 1. The separation conditions of the distillation column and the 1,3-BD recovery column are shown in Table 9 below.

TABLE 9

|  | Distillation column | 1,3-BD recovery column |
|---|---|---|
| Pressure (O/H) [kg/cm$^2$g] | 3.8 | 3.5 |
| Temp. (O/H) [° C.] | 42 | 41 |
| Temp. (BTM) [° C.] | 44 | 44 |
| Theoretical stage number | 80 | 56 |
| Reflux ratio | 111 | 2.2 |

As illustrated in FIG. 5A, the stream 316-1 derived from the overhead stream of the 1,3-BD fractionator was fed to the distillation column, and the overhead stream comprising water and a mixture of 1,3-BD and 1-butene was separated. Furthermore, the mixture of 1,3-BD and 1-butene was separated as a C4 mixture from the above overhead stream using the heat exchanger, and the remainder water 317-1 was transferred to the wastewater treatment unit.

The bottom stream 318-1 of the distillation column was transferred to the 1,3-BD recovery column, thus separating 1,3-BD as the overhead stream and 2-butene as the bottom stream. 1,3-BD in the separated overhead stream met commercial purity standards. As such, 1,3-BD was lost in an amount of about 5 wt % relative to the feed 316-1.

As shown in the above drawing, the dehydration products of 2,3-butanediol were separated through the above process, thereby obtaining 1,3-butadiene having a purity of 99.3% and methylethylketone having a purity of 99.9% at yields of 99.4% and 98.2%, respectively.

Example 3

In the dehydration of 2,3-butanediol as illustrated in FIG. 2A, a pilot test was performed to evaluate the actual performance of the reactor. The process conditions of the reactor for use in the pilot test are shown in Table 10 below.

TABLE 10

| Reactor | |
|---|---|
| Kind and dimension of reactor | Fixed-bed reactor<br>Diameter: 3 cm, Height: 1.3 m |

TABLE 10-continued

| Reactor | |
|---|---|
| Catalyst | Kind: Amorphous calcium phosphate catalyst (Ca/P molar ratio: 1.2)<br>Diameter: 2.85 mm, Weight: 80 g<br>Catalyst loading: loading in a space between 0.6 m from the top of the reactor and 0.3 m from the bottom thereof.<br>(SiC is packed in a space ranging from the top of the reactor to 0.6 m and a space ranging from the bottom of the reactor to 0.3 m) |
| Feed | 98.65 wt % of 2,3-butanediol |
| Process conditions | Pressure: 0.2 bar<br>Average temperature of catalyst bed: 348° C.<br>WHSV: 0.5 h$^{-1}$ |

The details of the inflow and outflow streams of the reactor are shown in Table 11 below. The performance of the reactor depending on the inflow and outflow streams of the reactor is given in Table 12 below.

TABLE 11

|  | Reactant (wt %) | Product (wt %) |
|---|---|---|
| 1,3-Butadiene | 0 | 28.14 |
| 1-Butene | 0 | 1.10 |
| 2-Butene | 0 | 0.75 |
| 2-Methyl Propanal | 0 | 3.92 |
| 3-Buten-2-ol | 0 | 0.75 |
| 2-Butanone (MEK) | 0 | 35.66 |
| 2,3-Butanediol | 98.65 | 0.84 |
| H$_2$O | 1.35 | 28.83 |

TABLE 12

|  | % |
|---|---|
| BDO conversion | 98.9 |
| BD selectivity | 28.4 |
| MEK selectivity | 36.0 |
| BD yield | 28.1 |

The performance of the reactor was similar to the performance of the reactor simulated using ASPEN PLUS of Example 1, and the products of the reactor were separated into the overhead stream comprising 1,3-BD-rich vapor and the bottom stream comprising MEK-rich liquid, which were then discharged.

Example 4

To evaluate the actual performance of the azeotropic distillation column as illustrated in FIG. 8A, a pilot test was performed. The process conditions for use in the pilot test are shown in Table 13 below.

TABLE 13

| Azeotropic distillation column | |
|---|---|
| Packing Column | Theoretical stage number: 56<br>Packing: Dixxon 3 mm |
| Supply stages | 15 stages |
| Process conditions | Pressure: 2.1 bar<br>Reflux: Organic phase total reflux<br>O/H Temp.: 16° C.<br>BTM Temp.: 103° C. |

The details of the inflow and outflow streams of the azeotropic distillation column are shown in Table 14 below.

TABLE 14

|  | Feed | Make-up entrainer | O/H | BTM |
|---|---|---|---|---|
| Temperature | 15 | 15 | 15.9 | 103.2 |
| Pressure [kg/cm²g] | 1.5 | 2 | 0.8 | 1.208 |
| Mass flow rate [kg/hr] | 1 | 0.0003 | 0.13 | 0.87 |
| 2-MPA | 0.129 |  | 0.004 | 0.125 |
| MEK | 0.753 |  | 0.008 | 0.745 |
| C-Hexane |  | 0.0003 | <0.001 | <0.001 |
| H₂O | 0.118 |  | 0.118 | trace |
| Mass fraction |  |  |  |  |
| 2-MPA | 0.129 |  | 0.032 | 0.144 |
| MEK | 0.753 |  | 0.062 | 0.856 |
| C-Hexane |  | 1 | 85 ppm | 335 ppm |
| H₂O | 0.118 |  | 0.906 | trace |

As is apparent from Table 14, the water in the feed was almost completely separated from the MEK-rich bottom stream through the overhead stream of the azeotropic distillation column.

Accordingly, simple modifications or variations of the present invention fall within the scope of the present invention as defined in the accompanying claims.

What is claimed is:

1. A method of recovering 1,3-butadiene and methylethylketone from dehydration products of 2,3-butanediol, comprising:
   a) dehydrating 2,3-butanediol in presence of an alkaline earth metal phosphate catalyst to provide a vapor stream comprising 1,3-butadiene, butene, methylethylketone, aldehyde, alcohol and water;
   b) cooling the vapor stream, thus separating a 1,3-butadiene-rich first vapor stream and a methylethylketone-rich first liquid stream;
   c) transferring the first vapor stream to a 1,3-butadiene purification unit, thus recovering 1,3-butadiene;
   d) subjecting the first liquid stream to phase separation, thus obtaining a second liquid stream as an organic phase and a third liquid stream as an aqueous solution phase, separately from c);
   e) separating the third liquid stream into (i) a water-rich bottom stream and (ii) a fourth liquid stream comprising a methylethylketone-water azeotropic mixture as an overhead stream;
   f) combining the second liquid stream and the fourth liquid stream, and removing water from the combined liquid stream, thus obtaining a fifth liquid stream, wherein f) is performed using an entrainer in an azeotropic distillation column, so that water is removed as an overhead stream and the fifth liquid stream is obtained as a bottom stream; and
   g) recovering methylethylketone from the fifth liquid stream.

2. The method of claim 1, wherein the dehydration products of 2,3-butanediol in a) contain at least 3.5 wt % of 1,3-butadiene and at least 3.5 wt % of methylethylketone.

3. The method of claim 1, further comprising scrubbing the 1,3-butadiene-rich first vapor stream, obtained in b), using a water-containing scrubbing fluid, before being fed to c).

4. The method of claim 3, wherein the water-containing scrubbing fluid is at least a portion of the water-rich bottom stream separated in e).

5. The method of claim 1, wherein c) comprises:
   c1) fractionating the first vapor stream, thus obtaining an overhead stream including 1,3-butadiene and butene;
   c2) transferring the overhead stream obtained in c1) to an extractive distillation column, thus separating a raffinate including butene as an overhead stream and an extract including 1,3-butadiene as a bottom stream; and
   c3) separating a mixture comprising 1,3-butadiene and water from the extract including 1,3-butadiene using at least one stripper.

6. The method of claim 5, wherein an extraction solvent used in the extractive distillation column in c2) includes an N-methyl-2-pyrrolidone (NMP) aqueous solution, and a concentration (water concentration) of the NMP aqueous solution exceeds 8 wt %.

7. The method of claim 6, wherein the concentration (water concentration) of the NMP aqueous solution exceeds 15 wt %.

8. The method of claim 5, wherein a weight ratio of the extraction solvent in c2) to the overhead stream obtained in c) ranges from 1:5 to 1:15.

9. The method of claim 5, wherein an amount of 1,3-butadiene in the extract is 4 to 20 wt %.

10. The method of claim 5, further comprising transferring the mixture comprising 1,3-butadiene and water, separated in c3), to a 1,3-butadiene purification column, so that water is removed as an overhead stream and 1,3-butadiene is recovered as a bottom stream, in which a water content in the recovered 1,3-butadiene is 100 wt ppm or less.

11. The method of claim 1, wherein the entrainer is cyclohexane.

12. The method of claim 1, wherein g) comprises:
   g1) fractionating the fifth liquid stream, thus separating a methylethylketone-containing bottom stream and an overhead stream containing a compound having a boiling point lower than that of methylethylketone; and
   g2) fractionating the methylethylketone-containing bottom stream obtained in g1), thus separating an overhead stream including methylethylketone and a bottom stream including a compound having a boiling point higher than that of methylethylketone.

13. The method of claim 1, wherein an amount of 1,3-butadiene in the first vapor stream is 65 to 95 wt %, and an amount of methylethylketone in the first liquid stream is 20 to 80 wt %.

14. The method of claim 5, wherein an amount of 1,3-butadiene in the overhead stream in c1) is 80 to 99.5 wt %.

15. The method of claim 5, wherein c3) is performed using a first stripper, and a second stripper operating at a pressure lower than the first stripper, and
   the second stripper is configured such that 1,3-butadiene contained in a bottom stream of the first stripper is additionally separated as an overhead stream and the overhead stream is recycled to the first stripper.

16. The method of claim 1, wherein c) comprises:
   c'1) fractionating the first vapor stream, thus obtaining an overhead stream including 1,3-butadiene and butene;
   c'2) transferring the overhead stream obtained in c'1) to a distillation column, thus separating, as an overhead stream, a mixture comprising 1-butene and 1,3-butadiene, and as a bottom stream, a mixture comprising 1,3-butadiene and 2-butene;
   c'3) recovering the mixture comprising 1-butene and 1,3-butadiene from the overhead stream separated in c'2); and
   c'4) transferring the bottom stream separated in c'2) to a 1,3-butadiene recovery column, thus separating 1,3-butadiene as an overhead stream and 2-butene as a bottom stream, and recovering the 1,3-butadiene.

17. The method of claim 16, wherein the overhead stream obtained in c'2) includes 80 to 95 wt % of 1,3-butadiene and 5 to 20 wt % of 1-butene, and the bottom stream obtained in c'2) includes 96 to 98.5 wt % of 1,3-butadiene and 0.5 to 3.5 wt % of 2-butene.

18. The method of claim 1, wherein the entrainer is used in an amount of 0.01 wt % or less relative to the combined liquid stream.

19. A method of preparing 1,3-butadiene and methylethylketone from 2,3-butanediol, comprising:
- a') fermenting a substrate comprising biomass, CO or $CO_2$ by a strain, thus producing 2,3-butanediol;
- b') subjecting the 2,3-butanediol to dehydration in presence of an alkaline earth metal phosphate catalyst, thus providing a vapor stream comprising 1,3-butadiene, butene, methylethylketone, aldehyde, alcohol and water;
- c') cooling the vapor stream, thus separating a 1,3-butadiene-rich first vapor stream and a methylethylketone-rich first liquid stream;
- d') transferring the first vapor stream to a 1,3-butadiene purification unit, thus recovering 1,3-butadiene;
- e') subjecting the first liquid stream to phase separation, thus obtaining a second liquid stream as an organic phase and a third liquid stream as an aqueous solution phase, separately from d');
- f') separating the third liquid stream into (i) a water-rich bottom stream and (ii) a fourth liquid stream comprising a methylethylketone-water azeotropic mixture as an overhead stream;
- g') combining the second liquid stream and the fourth liquid stream, and removing water from the combined liquid stream, thus obtaining a fifth liquid stream, wherein g') is performed using an entrainer in an azeotropic distillation column, so that water is removed as an overhead stream and the fifth liquid stream is obtained as a bottom stream; and
- h') recovering methylethylketone from the fifth liquid stream.

* * * * *